United States Patent
Petrovic et al.

(10) Patent No.: US 7,786,239 B2
(45) Date of Patent: Aug. 31, 2010

(54) MODIFIED VEGETABLE OIL-BASED POLYOLS

(75) Inventors: Zoran S. Petrovic, Pittsburg, KS (US); Ivan Javni, Pittsburg, KS (US); Alisa Zlatanic, Pittsburg, KS (US); Andrew Guo, Pittsburg, KS (US)

(73) Assignee: Pittsburg State University, Pittsburg, KS (US)

( * ) Notice: Subject to any disclaimer, the term of this patent is extended or adjusted under 35 U.S.C. 154(b) by 595 days.

(21) Appl. No.: 11/165,962

(22) Filed: Jun. 24, 2005

(65) Prior Publication Data

US 2006/0041157 A1  Feb. 23, 2006

Related U.S. Application Data

(60) Provisional application No. 60/583,302, filed on Jun. 25, 2004, provisional application No. 60/583,307, filed on Jun. 25, 2004.

(51) Int. Cl.
  C08G 83/00    (2006.01)
  C07D 303/00   (2006.01)
(52) U.S. Cl. ............ 528/1; 528/394; 528/403; 528/408; 528/486; 528/425; 554/149; 554/168; 549/513; 549/525
(58) Field of Classification Search ........... 528/1, 528/394, 403, 408, 486, 425; 554/149, 168; 549/513, 525
See application file for complete search history.

(56) References Cited

U.S. PATENT DOCUMENTS

| | | |
|---|---|---|
| 2,846,408 A | 8/1958 | Brachhagen et al. |
| 3,070,608 A | 12/1962 | Kuester et al. |
| 4,375,521 A | 3/1983 | Arnold |
| 4,423,239 A | 12/1983 | Miyazaki et al. |
| 4,508,853 A | 4/1985 | Kluth et al. |
| 4,546,120 A | 10/1985 | Peerman et al. |
| 4,551,517 A | 11/1985 | Herold et al. |
| 4,617,325 A | 10/1986 | Knobel et al. |
| 4,618,630 A | 10/1986 | Knobel et al. |
| 4,742,087 A | 5/1988 | Kluth et al. |
| 4,775,558 A | 10/1988 | Haas et al. |
| 4,806,571 A | 2/1989 | Knobel et al. |
| 4,826,944 A | 5/1989 | Hoefer et al. |
| 4,886,893 A | 12/1989 | Meffert et al. |
| 5,026,881 A | 6/1991 | Gruber |
| 5,032,323 A | 7/1991 | Virnig |
| 5,164,124 A | 11/1992 | Lange et al. |
| 5,266,714 A | 11/1993 | Stoll et al. |
| 5,302,626 A | 4/1994 | Hoefer et al. |
| 5,380,886 A | 1/1995 | Daute et al. |
| 5,382,647 A | 1/1995 | Daute et al. |
| 5,403,440 A | 4/1995 | Daute et al. |
| 5,442,082 A | 8/1995 | Uphues et al. |
| 5,482,647 A | 1/1996 | Bolkan et al. |
| 5,482,980 A | 1/1996 | Pcolinsky |
| 5,512,655 A | 4/1996 | Klauck et al. |
| 5,609,722 A | 3/1997 | Rodriguez et al. |
| 5,645,762 A | 7/1997 | Cook et al. |
| 5,688,989 A | 11/1997 | Daute et al. |
| 5,795,949 A | 8/1998 | Daute et al. |
| 6,046,298 A | 4/2000 | Beuer et al. |
| 6,057,375 A | 5/2000 | Wollenweber et al. |
| 6,107,433 A * | 8/2000 | Petrovic et al. ............ 528/1 |
| 6,180,686 B1 | 1/2001 | Kurth |
| 6,211,315 B1 | 4/2001 | Larock et al. |
| 6,258,869 B1 | 7/2001 | Shah et al. |
| 6,274,750 B1 | 8/2001 | Sato et al. |
| 6,359,023 B1 | 3/2002 | Kluth et al. |
| 6,399,698 B1 | 6/2002 | Petrovic et al. |
| 6,420,443 B1 | 7/2002 | Clark et al. |
| 6,433,121 B1 | 8/2002 | Petrovic et al. |
| 6,465,569 B1 | 10/2002 | Kurth |
| 6,495,611 B1 | 12/2002 | Arlt et al. |
| 6,548,609 B2 | 4/2003 | Ramirez-de-Arellano-Aburto et al. |
| 6,573,354 B1 | 6/2003 | Petrovic et al. |
| 6,583,302 B1 | 6/2003 | Erhan et al. |
| 6,610,811 B1 | 8/2003 | Westfechtel et al. |
| 6,649,667 B2 | 11/2003 | Clatty |
| 6,682,673 B1 | 1/2004 | Skwiercz et al. |
| 6,686,435 B1 | 2/2004 | Petrovic et al. |
| 6,864,296 B2 | 3/2005 | Kurth |
| 6,962,636 B2 | 11/2005 | Kurth et al. |
| 6,979,477 B2 | 12/2005 | Kurth et al. |
| 2002/0058774 A1 | 5/2002 | Kurth et al. |
| 2002/0061936 A1 | 5/2002 | Van Heumen et al. |

(Continued)

FOREIGN PATENT DOCUMENTS

EP     0 127 810     5/1984

(Continued)

OTHER PUBLICATIONS

International Search Report from International Patent Application No. PCT/US2005/022580, mailed Oct. 28, 2005, 2 pgs.

*Primary Examiner*—Duc Truong

(57) ABSTRACT

Methods of making unsaturated modified vegetable oil-based polyols are described. Also described are methods of making oligomeric modified vegetable oil-based polyols. An oligomeric composition having a modified fatty acid triglyceride structure is also described. Also, methods of making a polyol including hydroformylation and hydrogenation of oils in the presence of a catalyst and support are described.

25 Claims, 1 Drawing Sheet

U.S. PATENT DOCUMENTS

| | | |
|---|---|---|
| 2002/0099230 A1 | 7/2002 | Ramirez-de-Arellano-Aburto et al. |
| 2002/0119321 A1 | 8/2002 | Kurth et al. |
| 2002/0161161 A1 | 10/2002 | Heidbreder et al. |
| 2002/0192456 A1 | 12/2002 | Mashburn et al. |
| 2003/0083394 A1 | 5/2003 | Clatty |
| 2003/0088054 A1 | 5/2003 | Chasar et al. |
| 2003/0143910 A1 | 7/2003 | Mashburn et al. |
| 2003/0149214 A1 | 8/2003 | Westfechtel et al. |
| 2003/0166735 A1 | 9/2003 | Clatty |
| 2003/0191273 A1 | 10/2003 | Gertzmann et al. |
| 2003/0191274 A1 | 10/2003 | Kurth et al. |
| 2004/0082712 A1 | 4/2004 | Blount |
| 2005/0070620 A1 | 3/2005 | Herrington et al. |
| 2005/0121134 A9 | 6/2005 | Kurth et al. |
| 2005/0124709 A1 | 6/2005 | Krueger et al. |
| 2005/0131092 A1 | 6/2005 | Kurth et al. |
| 2005/0182228 A1 | 8/2005 | Kurth |
| 2006/0030632 A1 | 2/2006 | Krueger et al. |
| 2006/0041155 A1 | 2/2006 | Casper |
| 2006/0041156 A1 | 2/2006 | Casper et al. |
| 2006/0041157 A1 | 2/2006 | Petrovic et al. |

FOREIGN PATENT DOCUMENTS

| | | | |
|---|---|---|---|
| EP | 0 340 587 | | 4/1989 |
| EP | 0 361 080 | | 8/1989 |
| EP | 0 432 208 | | 6/1991 |
| EP | 0 554 590 | | 9/1992 |
| EP | 0 554 590 | | 8/1993 |
| EP | 0 600 958 | | 6/1994 |
| EP | 0 759 043 | | 2/2000 |
| GB | 877134 | | 8/1957 |
| GB | 2 428 677 | | 2/2007 |
| JP | 2004-244443 | | 2/2004 |
| SG | 55223 | | 12/1998 |
| WO | WO 92/07017 | | 4/1992 |
| WO | WO 97/07017 | | 4/1992 |
| WO | WO 97/21748 | | 6/1997 |
| WO | WO 01/25184 | | 4/2001 |
| WO | WO 01/70842 | | 9/2001 |
| WO | WO03/029182 | * | 4/2003 |
| WO | WO 03/078493 | | 5/2003 |
| WO | WO 2004/020497 | | 3/2004 |
| WO | WO 2004/063245 | | 7/2004 |
| WO | WO 2004/071281 | | 8/2004 |
| WO | WO 2004/096882 | | 11/2004 |
| WO | WO 2004/096883 | | 11/2004 |
| WO | WO 2005/000934 | | 1/2005 |
| WO | WO 2005/003202 | | 1/2005 |
| WO | WO 2005/078000 | | 8/2005 |
| WO | WO 2005/123798 | | 12/2005 |
| WO | WO 2006/012344 | | 2/2006 |
| WO | WO 2006/047431 | | 5/2006 |
| WO | WO 2006/047432 | | 5/2006 |
| WO | WO 2006/047433 | | 5/2006 |
| WO | WO 2006/047434 | | 5/2006 |
| WO | WO 2006/065345 | | 6/2006 |
| WO | WO 2006/071549 | | 7/2006 |
| WO | WO 2006/116456 | | 11/2006 |
| WO | WO 2006/118995 | | 11/2006 |
| WO | WO 2007/019051 | | 2/2007 |
| WO | WO 2007/019063 | | 2/2007 |

* cited by examiner

MODIFIED VEGETABLE OIL-BASED POLYOLS

CROSS-REFERENCE TO RELATED APPLICATIONS

This application claims priority from U.S. Provisional Application Ser. No. 60/583,302, filed on Jun. 25, 2004, and U.S. Provisional Application Ser. No. 60/583,307, filed on Jun. 25, 2004, both of which are incorporated in their entirety in this application by reference.

TECHNICAL FIELD

This invention relates to vegetable oil-based polyols.

BACKGROUND

Polyols are generally produced from petroleum. Polyols are useful in a variety of applications, as polyols may be used in coatings, adhesives, sealants, elastomers, resins and foams. Polyols may be used in a wide variety of fields including the textile, plastic, medical, chemical, manufacturing, and cosmetic industries.

Research in recent years has focused on alternative, non-petroleum based sources of polyols. One area of focus has been the production of polyols from natural oils, with vegetable oils being of particular focus.

Some examples of non-petroleum based polyols include those described by Petrovic et al. in U.S. Pat. Nos. 6,107,433, 6,433,121, 6,573,354, and 6,686,435. Another example is described in Kurth, U.S. Pat. No. 6,180,686.

SUMMARY

Modified vegetable oil-based polyols are described that include unreacted double bonds. Additionally, partially epoxidized vegetable oils, which also include unreacted double bonds, are described.

In one aspect, a method of making an unsaturated modified vegetable oil-based polyol is described, including reacting a partially epoxidized vegetable oil, a proton donor, and fluoroboric acid to form the unsaturated modified vegetable oil-based polyol.

In a further embodiment, the method also includes neutralizing the unsaturated modified vegetable oil-based polyol. In some instances, neutralizing includes the addition of $Ca(OH)_2$, CaO, hydrotalcite, ammonium carbonate, diethanolamine, triethanolamine, or alkali or alkaline earth hydroxides.

In a further embodiment, the method also includes reacting a vegetable oil with a peroxyacid under reaction conditions that epoxidize less than 100% of the double bonds of the vegetable oil available for reaction to form the partially epoxidized vegetable oil. In some instances, the reactions are performed without purification between the reactions.

In some embodiments, the proton donor includes alcohol. Variously, the alcohol includes a polyol or includes methanol. In other embodiments, the proton donor includes water. The reaction may proceed for less than about 5 hours, less than about 3 hours, proceeds for about 60 minutes or less, or may proceed for about 20 to about 40 minutes.

In some instances, the unsaturated modified vegetable oil-based polyol has a substantially preserved triglyceride structure.

Variously, the unsaturated modified vegetable oil-based polyol has a viscosity measured at 25° C. from about 0.05 Pa·s to about 12.0 Pa·s. The unsaturated modified vegetable oil-based polyol may have a hydroxyl number from about 20 to about 300 mg KOH/g polyol. The unsaturated modified vegetable oil-based polyol may have a functionality from about 1.0 to about 6.0. The unsaturated modified vegetable oil-based polyol may have an iodine value from about 5 to about 120. The unsaturated modified vegetable-oil based polyol may have a Gardner color value of less than about 3.0. The unsaturated modified vegetable-oil based polyol may have a Gardner color value of less than about 2.5.

In some embodiments, the fluoroboric acid is self-regulating.

Variously, the unsaturated modified vegetable oil-based polyol may have an epoxy oxygen content (EOC) from about 0% to about 3%. Or, the unsaturated modified vegetable oil-based polyol may have an epoxy oxygen content (EOC) from about 0% to about 0.1%.

In another aspect, a method of preparing a polyol including combining a partially epoxidized vegetable oil, alcohol, and a catalytic amount of acid to form the unsaturated modified vegetable oil-based polyol is described. Optionally, water may be present. Preferably, the acid is fluoroboric acid.

In another aspect, a method of making an oligomeric modified vegetable oil-based polyol is described, including reacting a mixture including an epoxidized vegetable oil and a ring opener to form an oligomeric modified vegetable oil-based polyol, wherein the oligomeric modified vegetable oil-based polyol comprises at least about 20% oligomers, and a viscosity at 25° C. of less than about 8 Pa·s.

In some embodiments, the mixture also includes an acid. In some instances, the acid includes fluoroboric acid. In some cases, the fluoroboric acid is self-regulating. In other instances, the acid includes carboxylic acids, Lewis acids, and Bronsted-Lowry inorganic acids.

In some embodiments, the oligomeric modified vegetable oil-based polyol includes at least about 40% oligomers. In some embodiments, the oligomeric modified vegetable oil-based polyol includes at least about 50% oligomers.

In various embodiments, the ring opener includes alcohol. In some cases, the alcohol includes a branched alcohol. In other cases, the alcohol includes a linear alcohol. In some embodiments, the ring opener includes a vegetable-oil based polyol. In some embodiments, the ring opener includes a proton donor. In some embodiments, the ring opener includes hydroxyl groups, and wherein the ratio of hydroxyl groups present in the ring opener to epoxy groups present in the epoxidized vegetable oil is from about 0.1 to about 1.0.

In some embodiments, the method also includes blending petrochemical-based polyols with the epoxidized vegetable oil and the ring opener so that said petrochemical-based polyols also undergo the polymerization reaction.

In some embodiments, the epoxidized vegetable oil includes essentially full epoxidation of all unsaturated groups present in the vegetable oil. In others, the epoxidized vegetable oil includes less than about 90% epoxidation of all unsaturated groups present in the vegetable oil. In others, the epoxidized vegetable oil includes less than about 80% epoxidation of all unsaturated groups present in the vegetable oil. In some cases, the oligomeric modified vegetable oil-based polyol has residual epoxide functionality. In other cases, the oligomeric modified vegetable oil-based polyol has residual olefinic functionality. In other cases, the oligomeric modified vegetable oil-based polyol has residual epoxide functionality and has residual olefinic functionality.

Variously, the oligomeric modified vegetable oil-based polyol may have a functionality from about 1.0 to about 6.0. The oligomeric modified vegetable oil-based polyol may have a hydroxyl number from about 20 to about 300 mg KOH/g polyol. The oligomeric modified vegetable oil-based polyol may have a number average molecular weight from about 1,200 to about 8,000. The oligomeric modified vegetable oil-based polyol may have a weight average molecular weight from about 1500 to about 50,000.

In some embodiments, the epoxidized vegetable oil is formed in situ from a vegetable oil in the presence of an acid.

In some embodiments, the method includes ring-opening the epoxidized vegetable oil using an alcohol and an acid catalyst, and reacting an epoxidized vegetable oil with the ring-opened epoxidized vegetable oil.

In another aspect, a method of making an oligomeric modified vegetable oil-based polyol is described, including reacting a mixture comprising an epoxidized vegetable oil, fluoroboric acid, and a ring opener to form an oligomeric modified vegetable oil-based polyol.

In another aspect, a method of making an oligomeric modified vegetable oil-based polyol is described, including reacting a mixture comprising an epoxidized vegetable oil and a ring opener to form an oligomeric modified vegetable oil-based polyol, wherein the oligomeric modified vegetable oil-based polyol comprises at least about 40% oligomers.

In another aspect, a method of making an oligomeric modified vegetable oil-based polyol is described, including reacting a mixture comprising an epoxidized vegetable oil, an acid catalyst, and a polyol to form an oligomeric modified vegetable oil-based polyol.

In various aspects, methods of making oligomeric modified vegetable oil-based polyols are described, including cationically polymerizing an epoxidized vegetable oil in the presence of an acid catalyst, or reacting a polyol with an epoxidized vegetable oil, or combining a modified vegetable oil-based polyol, a catalytic amount of acid, and an epoxidized vegetable oil to form the oligomeric modified vegetable oil-based polyol.

In another aspect, a method of making a polyol is described, including reacting an epoxidized vegetable oil with a ring opener to form a modified vegetable oil-based polyol, wherein the ring opener is a reduced hydroformylated compound. In some embodiments, the reduced hydroformylated compound includes a reduced hydroformylated vegetable oil-based polyol. In another embodiment, the reduced hydroformylated compound includes reduced hydroformylated methyl esters of fatty acids.

In another aspect, a method of making a polyol is described, including hydroformylating a vegetable oil to form an aldehydic intermediate in the presence of a catalyst, and hydrogenating the aldehydic intermediate to form a polyol in the presence of the catalyst and a support. In some embodiments, the method also includes activating a catalyst comprising metal on a support to form a catalyst comprising a metal carbonyl.

In some embodiments, the catalyst on a support is in an organic media. The organic media may be recovered after the hydrogenation step. The organic media may be recovered by vacuum stripping. In some embodiments, the organic media includes aromatics, hydrocarbons, or combinations thereof. Variously, the organic media includes hexanes, heptanes, benzene, toluene, acetone, chloroform, methanol, ethanol, isopropanol, butanol, ethyl acetate, and combinations thereof.

In some embodiments, the catalyst, the support, and an organic media are recovered after the hydrogenation step. Some embodiments may include mixing the recovered catalyst, support and organic media together under conditions to re-activate the catalyst. The re-activated catalyst may be used in hydroformylation and hydrogenation reactions.

The catalyst may include a metal, or a metal carbonyl. In some embodiments, the metal comprises a transition metal within Group VIIIB of the periodic chart. In some embodiments, the metal carbonyl includes cobalt carbonyl.

In some embodiments, the support includes carbon black. Variously, the support includes carbon black, alumina, silica, $TiO_2$, MgO, ZnO, $CaCO_3$, $CaSO_4$, $MgSO_4$, or combinations thereof.

In some embodiments, the hydroformylation step takes place at a pressure of about 1000-5000 psig of gas and at a temperature from about 100° C. to about 300° C. The gas may be syngas including carbon monoxide and hydrogen.

The method may include recovering the catalyst on a support after the hydrogenation step. The catalyst may be attached to the support. The recovered catalyst on a support is reused in hydroformylation and hydrogenation reactions. The catalyst may be recovered by filtration.

In another aspect, a method of making a polyol is described, including hydroformylating an oil to form an aldehydic intermediate using a catalyst, and hydrogenating the aldehydic intermediate to form a polyol using the same catalyst in the presence of a support. The catalyst and the support may be added prior to hydroformylation. In another approach, the catalyst may be added prior to hydroformylation, and the support may be added prior to hydrogenation. Some embodiments also include recovering the catalyst and support following hydrogenation for use in hydroformylation.

The details of one or more embodiments of the invention are set forth in the description below. Other features, objects, and advantages of the invention will be apparent from the description, the drawing, and the claims.

DETAILED DESCRIPTION

Terms and Definitions

Figure 1:
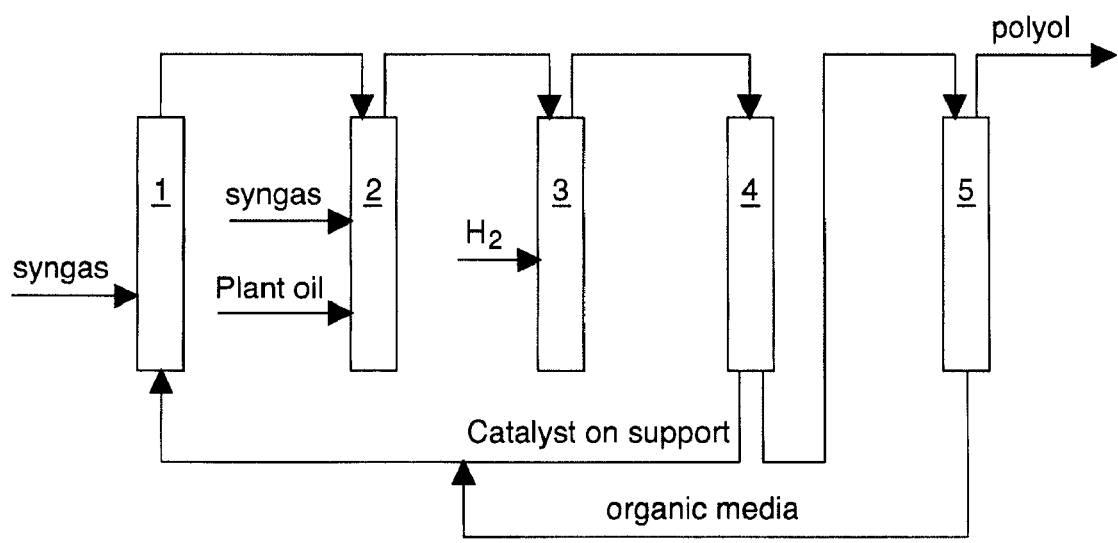
FIG. 1 is a schematic illustration of one embodiment of the invention.

As used herein, "polyol" refers to a molecule having an average of greater than 1.0 hydroxyl groups per molecule. It may also include other functionalities.

As used herein, "modified vegetable oil-based polyol" refers to a non-naturally occurring polyol prepared by treating a vegetable oil so as to modify the chemical structure of the vegetable oil, thereby yielding the polyol.

As used herein, "partially epoxidized vegetable oil" refers to a non-naturally occurring oil prepared by treating a vegetable oil so as to modify the chemical structure of the molecule to epoxidize some but not all of the double bonds present in the vegetable oil.

As used herein, "unsaturated modified vegetable oil-based polyols" refers to vegetable oil-based polyols having residual double bonds.

As used herein, "oligomeric modified vegetable oil-based polyol" refers to a polyol that has at least two triglyceride-based monomer units present. It is also referred to as an "oligomeric polyol."

As used herein, "EOC" refers to epoxy oxygen content, which is the weight of epoxy oxygen per molecule, expressed in %.

Partially Epoxidized Vegetable Oil

A partially epoxidized vegetable oil may be prepared by a method that includes reacting a vegetable oil with a peroxyacid under conditions that convert less than 100% of the double bonds of the vegetable oil to epoxide groups. Typically, the method will also include combining another acid with the vegetable oil and peroxyacid components to form a mixture that reacts to form a partially epoxidized vegetable oil. The partially epoxidized vegetable oil may include at least about 10%, at least about 20%, at least about 25%, at least about 30%, at least about 35%, at least about 40% or more of the original amount of double bonds present in the vegetable oil. The partially epoxidized vegetable oil may include up to about 90%, up to about 80%, up to about 75%, up to about 70%, up to about 65%, up to about 60%, or fewer of the original amount of double bonds present in the vegetable oil.

One component of the reaction mixture is a vegetable oil. Examples of suitable vegetable oils include soybean oil, safflower oil, linseed oil, corn oil, sunflower oil, olive oil, canola oil, sesame oil, cottonseed oil, palm oil, rapeseed oil, tung oil, fish oil, peanut oil, and combinations thereof. Natural vegetable oils may be used, and also useful are partially hydrogenated vegetable oils and genetically modified vegetable oils, including high oleic safflower oil, high oleic soybean oil, high oleic peanut oil, high oleic sunflower oil, and high erucic rapeseed oil (crambe oil). The number of double bonds present in a vegetable oil may be measured, and iodine value (IV) is a measure of the number of double bonds per molecule. One double bond per molecule roughly corresponds to an iodine value of 28. For example, commercially available soybean oil typically has around 4.6 double bonds/molecule, and typically has an iodine value of 127-140. Canola oil typically has an iodine value around 115, corresponding to about 4.1 double bonds/molecule. In general, the iodine values for the vegetable oils used will range from about 40 to about 240. Preferably, oils having an iodine value greater than about 80, greater than about 100, or greater than about 110 will be used. Preferably, oils having an iodine value less than about 240, less than about 200, or less than about 180 will be used.

Another component of the reaction mixture is a peroxyacid. Examples of peroxyacids that may be used include peroxyformic acid, peroxyacetic acid, trifluoroperoxyacetic acid, benzyloxyperoxyformic acid, 3,5-dinitroperoxybenzoic acid, m-chloroperoxybenzoic acid, and combinations thereof. Preferably, peroxyformic acid or peroxyacetic acid will be used. The peroxyacids may be added directly to the reaction, or may be formed in-situ by reacting a hydroperoxide with a corresponding acid such as formic acid, benzoic acid, fatty acids such as oleic acid, or acetic acid. Examples of hydroperoxides that may be used include hydrogen peroxide, tert-butylhydroperoxide, tripheylsilylhydroperoxide, cumylhydroperoxide, and combinations thereof. Most preferably, hydrogen peroxide will be used. Preferably, the amount of acid used to form the peroxyacid is from about 0.25 to about 1.0 moles of acid per mole of double bonds in the vegetable oil, and more preferably from about 0.45 to about 0.55 moles of acid per mole of double bonds in the vegetable oil. Preferably, the amount of hydroperoxide used to form the peroxy acid is 0.5 to 1.5 moles of hydroperoxide per mole of double bonds in the vegetable oil, and more preferably 0.8 to 1.2 moles of hydroperoxide per mole of double bonds in the vegetable oil.

Typically, an additional acid component will also be present in the reaction mixture. Examples of suitable additional acids include sulfuric acid, toluenesulfonic acid, trifluoroacetic acid, fluoroboric acid, Lewis acids, acidic clays, or acidic ion exchange resins.

Optionally, a solvent may be added to the reaction. Suitable solvents include chemically inert solvents such as aprotic solvents. For example, these solvents do not include a nucleophile, and are non-reactive with acids. Hydrophobic solvents, such as aromatic and aliphatic hydrocarbons, are especially desirable. Examples of suitable solvents include benzene, toluene, xylene, hexane, pentane, heptane, and chlorinated solvents such as carbon tetrachloride. Preferably toluene will be used if a solvent is used in the reaction mixture. Solvents are useful in that they may be used to reduce the speed of the reaction or to reduce the number of side chain reactions. In general, a solvent also acts as a viscosity reducer for the resulting composition.

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Examples of neutralizing agents that may be used include ammonia, calcium carbonate, sodium bicarbonate, magnesium carbonate, amines, and resins, as well as aqueous solutions of neutralizing agents. Preferably, the neutralizing agent will be an anionic ion-exchange resin. An example of a suitable weakly-basic ion-exchange resin is Lewatit MP-64 ion-exchange resin (available from Bayer). If a solid neutralizing agent, such as an ion-exchange resin, is used, the oil may be filtered to remove the neutralizing agent after neutralization. Alternatively, the reaction mixture may be neutralized by passing the mixture through a neutralization bed containing a resin or other materials. Alternatively, the reaction product may be repeatedly washed to separate and remove the acidic components from the product. In addition, one or more of the processes may be combined in neutralizing the reaction product. For example, the product could be washed, neutralized with a resin material, and then filtered.

Subsequent to the epoxidation reaction, excess solvents may be removed from the reaction product (partially epoxidized vegetable oil). These excess solvents may be solvents given off by the reaction, or those added to the reaction. The excess solvents may be removed by separation, vacuum, or other method. Preferably, the excess solvent removal will be accomplished by exposure to low vacuum.

Vegetable oils of the type described herein typically are composed of triglycerides of fatty acids. These fatty acids may be either saturated, monounsaturated or polyunsaturated and contain varying chain lengths ranging from $C_{12}$ to $C_{24}$. The most common fatty acids include saturated fatty acids such as lauric acid (dodecanoic acid), myristic acid (tetradecanoic acid), palmitic acid (hexadecanoic acid), steric acid (octadecanoic acid), arachidic acid (eicosanoic acid), and lignoceric acid (tetracosanoic acid); unsaturated acids include such fatty acids as palmitoleic (a C16 acid), and oleic acid (a C18 acid); polyunsaturated acids include such fatty acids as linoleic acid (a di-unsaturated C18 acid), linolenic acid (a tri-unsaturated C18 acid), and arachidonic acid (a tetra-unsubstituted C20 acid). The triglyceride oils are comprised of esters of these fatty acids in random placement onto the three sites of the trifunctional glycerine molecule. Different vegetable oils will have different ratios of these fatty acids and within a given vegetable oil there is a range of these acids as well depending on such factors as where the vegetable or crop is grown, maturity of the vegetable or crop, the weather during the growing season, etc. Because of this it is difficult to have a specific or unique structure for any given vegetable oil, but rather a structure is typically based on some statistical average. For example soybean oil contains a mixture of stearic acid, oleic acid, linoleic acid, and linolenic acid in the ratio of 15:24:50:11, this translates into an average molecular weight of approximately 800-860 daltons and an average number of double bonds of 4.4-4.7 per triglyceride. One method of quantifying the number of double bonds is the iodine value (IV) which is defined as the number of grams of iodine that will react with 100 grams of vegetable oil. Therefore for soybean oil, the average iodine value range from 120-140.

Various embodiments of fully or partially epoxidized vegetable triglyceride oils have the following generic chemical structure:

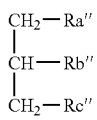

Wherein Ra", Rb", and Rc" are independently selected from the fatty acid materials described above. Materials of this type are the starting materials for one embodiment of the present invention. In another embodiment these starting materials are converted by peroxyacids to fully or partially epoxidized vegetable oils. Ra" is composed of —(CO)Za"; Rb" is composed of —(CO)Zb"; and Rc" is composed of —(CO)Zc". Wherein Za", Zb", Zc" independently comprise C15 to C17 linear carbon chains. These linear carbon chains are comprised methylene units, 2,3-oxiranyl units, 1,2-ethenediyl units, or combinations thereof, and further comprising an endcap methyl group.

Typical examples of Za", Zb", and Zc" include

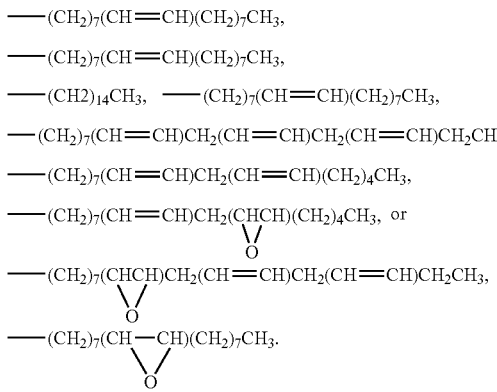

For the purpose of this patent the methylene group is defined as —CH$_2$—; 2,3-oxiranyl is defined as

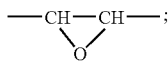

and 1,2-ethenediyl is defined as —CH=CH—.

Unsaturated Modified Vegetable Oil-Based Polyols

Unsaturated modified vegetable oil-based polyols may be prepared by combining a partially epoxidized vegetable oil with a ring opener and an acid.

Suitable partially epoxidized vegetable oils may be prepared as described above.

A ring opener will be used to open the epoxide rings in the partially epoxidized vegetable oil to form the unsaturated modified vegetable oil-based polyol. Various ring-openers may be used including proton donors such as alcohols and water (including residual amounts of water). Preferably, an alcohol will be used. Examples of suitable alcohols that may be used in the reaction mixture forming the unsaturated modified vegetable oil-based polyols include methanol, ethanol, propanol, isopropanol, butanol, and mixtures thereof. Preferably, methanol, ethanol, or a mixture thereof will be used. More preferably, methanol will be used. In addition, higher order alcohols may be used as ring openers, including polyols described elsewhere in this application.

In addition to other ring openers, such as an alcohol, water may optionally be present in the reaction mixture.

Examples of suitable acids for use in the reaction mixture include sulfuric acid and fluoroboric acid. Preferably, fluoroboric acid will be used. The amount of acid used will preferably be at least 0.01%, at least 0.02%, or at least 0.05% by weight of the total reaction mixture. The amount of acid used will preferably be less than about 0.5%, less than about 0.3%, or less than about 0.2% by weight of the total reaction mixture.

The reaction mixture may be heated as the components are added together, or after the components have been combined. Preferably, the reaction mixture will initially be heated to a temperature at least about 35° C., or at least about 50° C. Preferably, the reaction mixture will be heated to a temperature less than about 120° C., less than about 100° C., less than about 80° C., or less than about 70° C. There may be some reaction of components during this heating.

After reaching the desired temperature, the reaction will proceed for an additional length of time. Suitably, the reaction will proceed for a period of time ranging from 10 minutes to 12 hours or longer. Preferably, the reaction will proceed for an additional 10 minutes or longer, 20 minutes or longer, or 30 minutes or longer. Preferably, the reaction will proceed for an additional 5 hours or less, 3 hours or less, 100 minutes or less, 75 minutes or less, 60 minutes or less, or 40 minutes or less. During this additional reaction time, the temperature of the reaction mixture may reach a temperature about 40° C. or higher, or about 60° C. or higher. The reaction mixture may reach a temperature about 100° C. or less, or about 80° C. or less. In general, the temperature of the reaction may be controlled by a solvent or alcohol boiling point, or controlled from outside the reaction using a temperature control system, such as a water bath.

After this additional reaction time, the temperature of the reaction mixture may be reduced.

Following the reaction, the catalyst may be neutralized. A neutralizing agent may be added to neutralize any remaining acidic components in the reaction product. Suitable examples of neutralizing agents include weak bases, metal bicarbonates, basic clays, or ion-exchange resins. Examples of suitable neutralizing agents include ammonia, calcium carbonate, calcium hydroxide, calcium oxide, hydrotalcite, ammonium carbonate, diethanolamine, triethanolamine, sodium bicarbonate, magnesium carbonate, amines, alkali or alkaline earth hydroxides, and ion-exchange resins. The neutralizing agent may be prepared in a mixture before addition, such as in an aqueous slurry or aqueous solution. Preferably, a basic ion-exchange resin will be used as the neutralizing agent. An example of a suitable ion-exchange resin is Lewatit MP-64 ion-exchange resin. The amount of neutralizing agent preferably is sufficient to ensure that essentially no free acid remains. If ammonium carbonate is used, the amount of ammonium carbonate preferably ranges from 0.05-1% by weight of the mixture, and more preferably from 0.1-0.2% by weight. If a solid neutralizing agent, such as an ion-exchange resin, is used, the oil may be filtered to remove the neutralizing agent after neutralization. Alternatively, the reaction mixture may be neutralized by passing the mixture through a neutralization bed containing a resin or other materials. Alternatively, the reaction product may be repeatedly washed to separate and remove the acidic components from the product. In addition, one or more of the processes may be combined in neutralizing the reaction product, and more than one neutralizing agent may be used. For example, the polyol product could be washed, neutralized with a resin material, and then filtered.

Following the reaction, remaining excess components other than the reaction product, such as remaining ring opener components or components given off by the reaction, may be removed from the reaction product. These excess components may be removed by separation, vacuum, or other method. Preferably, the excess components will be removed by exposure to low vacuum.

The unsaturated modified vegetable oil-based polyols may have a range of desired characteristics depending upon various parameters including the components used, the reaction time, the reaction temperature, and the concentration of the ring opener. However, in general, the unsaturated modified vegetable oil-based polyols will have a viscosity from about 0.05 Pa·s to about 12.0 Pa·s (at 25° C.). Preferably, the unsaturated modified vegetable oil-based polyols will have a viscosity from about 0.1 Pa·s to about 3.0 Pa·s, and more preferably to about 2.0 Pa·s (at 25° C.). Without intending to be bound by any theory, it is believed that the viscosity of these polyols is low because the method avoids substantial side reactions such as polymerization and cross-linking.

Typically, the unsaturated modified vegetable oil-based polyols will have a hydroxyl number from about 20 mg KOH/g to about 300 mg KOH/g. Preferably, the unsaturated modified vegetable oil-based polyols will have a hydroxyl number at least about 50 mg KOH/g or higher, or at least about 75 mg KOH/g or higher. Preferably, the unsaturated modified vegetable oil-based polyols will have a hydroxyl number about 200 mg KOH/g or lower, or about 180 mg KOH/g or lower.

In general, the unsaturated modified vegetable oil-based polyols will have an acid number from about 0.1 mg KOH/g to about 3.0 mg KOH/g. In general, the unsaturated modified vegetable oil-based polyols will have a number average functionality of about 0.5 or greater, or about 1.0 or greater. Typically, the unsaturated modified vegetable oil will have a number average functionality of less than about 10.0, or less than about 6.0.

Generally, the unsaturated modified vegetable oil-based polyols will have a color value, using the Gardner color scale, of less than about 3.0. Preferably, the unsaturated modified vegetable oil-based polyols will have a Gardner color value of less than about 2.5. The Gardner Scale is a visual scale, and is described in ASTM D1544, "Standard Test Method for Color of Transparent Liquids (Gardner Color Scale)" and ASTM D6166, "Standard Test Method for Color of Naval Stores and Related Products (Instrumental Determination of Gardner Color)." The Gardner scale ranges colors from light yellow to red defined by the chromaticities of glass standards numbered from 1 for the lightest to 18 for the darkest. The scale is used for chemicals and oils including resins, varnishes, lacquers, drying oils, fatty acids, lecithins, sunflower oil and linseed oil.

Typically, the unsaturated modified vegetable oil-based polyols will have an iodine value in the range from about 5 g $I_2$/100 g to about 150 g $I_2$/100 g. Preferably, the unsaturated modified vegetable oil-based polyols will have an iodine value of about 10 g $I_2$/100 g or higher, or about 30 g $I_2$/100 g or higher. Preferably, the unsaturated modified vegetable oil-based polyols will have an iodine value of about 100 g $I_2$/100 g or lower, or about 80 g $I_2$/100 g or lower.

Various embodiments of unsaturated modified vegetable-oil based polyols have the following generic chemical structure:

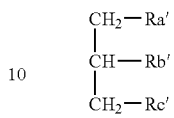

wherein Ra', Rb', and Rc' are independently derived from the partially epoxidized vegetable triglyceride oils materials described above. Materials of this type are the starting materials for one embodiment of the present invention. In another embodiment these starting materials are converted by peroxy acids to partially epoxidized vegetable oils. Ra' is composed of —(CO)Za'; Rb' is composed of —(CO)Zb'; and Rc' is composed of —(CO)Zc'. Wherein Za', Zb', Zc', are independently comprise C15 to C17 linear carbon chains. These linear carbon chains are comprised methylene units, vicinal hydroxymethylenealkoxymethylene units, 2,3-oxiranyl units, 1,2-ethenediyl units, or combinations thereof, and further comprising an endcap methyl group.

Za', Zb', and Zc' are each independently selected from the group consisting of

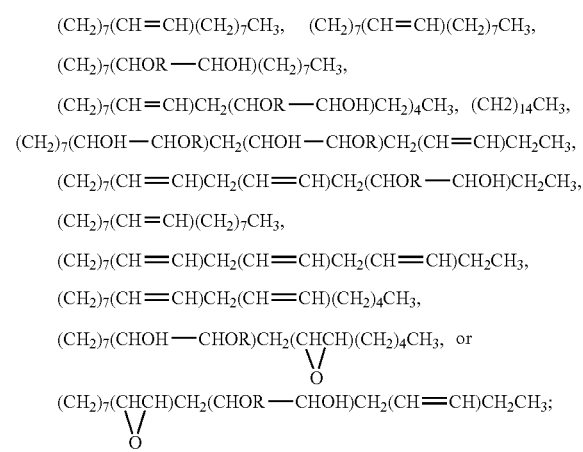

wherein R comprises H, $C_1$-$C_{10}$ alkyl groups, $C_7$-$C_{15}$ alkaryl, alkoxyalkyl, or alkylaminoalkyl groups and combinations thereof.

For the purpose of this patent the methylene group is defined as —$CH_2$—; 2,3-oxiranyl is defined as

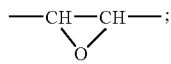

and 1,2-ethenediyl is defined as —CH=CH—;

and vicinal hydroxymethylenealkoxymethylene is defined as —CH(OH)—CH(OR)— wherein R comprises hydroxyl, alkoxy and substituted alkoxys. In general, an unsaturated modified vegetable-oil based polyol will include at least one 1,2-ethenediyl unit. In addition, the total number of 2,3-oxiranyl units and vicinal hydroxymethylenealkoxymethylene units and 1,2-ethenediyl units will generally be approximately equal to the original number of double bonds found in the starting vegetable oil prior to epoxidation and ring opening.

Oligomeric Polyols

Oligomeric modified vegetable oil-based polyols may be prepared from a reaction mixture including an epoxidized vegetable oil, a ring opener, and acid.

The first component is an epoxidized vegetable oil. The epoxidized vegetable oil may be fully epoxidized or partially epoxidized. Both saturated and unsaturated epoxidized vegetable oils can be used. Using saturated epoxidized vegetable oils having residual epoxy groups leads to oligomeric polyols having good oxidative stability. It is also believed that the use of unsaturated epoxidized vegetable oils creates oligomeric polyols having a lower viscosity compared to products prepared using saturated epoxidized vegetable oils.

If a solvent was used in the mixture forming the epoxidized vegetable oil, generally the solvent will be removed before use in an oligomerization reaction. Generally, excess reactants from any preliminary reactions are also removed prior to the oligomerization reaction.

The second component of the reaction mixture is an acid. The preferred acid catalyst is fluoroboric acid. The acid will preferably be present in an amount from about 0.01 to about 0.3% by weight, based upon the total weight of the reaction mixture, and more preferably is present in an amount from about 0.05 to about 0.15% by weight.

The third component is a ring opener, which acts as a proton donor. Various ring-openers may be used including alcohols, water (including residual amounts of water), and other compounds having one or more nucleophilic groups. Combinations of ring-openers may be used. Preferably an alcohol will be used. Examples of suitable alcohols include methanol, ethanol, propanol, isopropanol, butanol, polyols, and vegetable oil-based polyols. Suitable vegetable-oil based polyols include hydroformylated vegetable oil based polyols, partially epoxidized vegetable oil-based polyols, and unsaturated modified vegetable oil-based polyols. The ring opener might be reduced hydroformylated compounds. Suitable reduced hydroformylated compounds include derivatives of reduced hydroformylated fatty acids. Examples of suitable derivatives of reduced hydroformylated fatty acids include esters, amides, and salts, such as reduced hydroformylated methyl esters of fatty acids. The ring opener could be trace amounts of water present in a reaction mixture. Under some conditions, the acid present in the reaction mixture might act as a ring opener.

If an alcohol is used as a ring opener, preferably the ratio of the moles of hydroxyl groups to moles of epoxide groups present range from 0.1 to 1.0. More preferably the ratio will range from 0.3 to 0.6 moles hydroxyl groups to moles epoxide groups.

Optionally, a solvent may be added to the reaction mixture. Any aprotic solvent such as toluene, benzene, xylene, hexane, heptane, or chlorinated solvent would serve as a suitable solvent. In general, a solvent acts as a viscosity reducer for the resulting composition.

Optionally, water may also be present in addition to any other ring-opener. If present, the amount of water may be greater than about 0.1% by weight based upon the total weight of the reaction mixture, greater than about 1% by weight, greater than about 5% by weight, or greater than about 10% by weight. If present, the amount of water may be less than about 25% by weight, less than about 20% by weight, or less than about 15% by weight.

If a vegetable oil-based polyol and an epoxidized vegetable oil are used in the reaction mixture, the ratio of the modified vegetable oil-based polyol to the epoxidized vegetable oil affects the molecular weight of the resulting oligomeric polyol. If both are used, preferably the ratio of the moles of hydroxyl groups to moles of epoxide groups present range from 0.2 to 1.0, and more preferably range from 0.25 to 0.5 moles hydroxyl groups to moles epoxide groups.

The reaction may proceed for a period of time of at least 10 minutes. Typically, the reaction will proceed for a period of time from about 30 minutes to about 10 hours. Preferably, the reaction time will be from about 1 hour to about 3 hours. Typically, the reaction will be conducted at a temperature from about 25° C. to about 100° C. Preferably, the temperature of the reaction will be from about 50° C. to about 100° C. In general, it has been observed that the reaction proceeds quickly at a temperature in the range between 50 and 100° C.

Less ring opener may be used when the reaction is carried out at a higher temperature. However, using a lower amount of ring opener may lead to a vegetable oil-based oligomerized polyol having a lower acid number than one made using a higher ring opener concentration in the reaction mixture.

In general, the unsaturated modified vegetable oil-based polyols may have a range of desired characteristics depending upon various parameters including the components used, the reaction time, the reaction temperature, and the concentration of the ring opener.

However, the resulting oligomeric modified vegetable oil-based polyols may typically have a number average molecular weight greater than about 1200. Preferably, the polyols will have a number average molecular weight greater than about 1500 or greater than about 2000. Preferably, the polyols will have a number average molecular weight less than about 5000. Typically, the resulting oligomeric modified vegetable oil-based polyols will have a weight average molecular weight ranging from about 2000 to about 50,000. In general, the weight average molecular weight will be about 2 to about 10 times greater than the number average molecular weight. Also, the viscosity of the oligomeric polyols changed to some degree according to oligomer content.

Preferably, the resulting oligomeric polyol will also have a hydroxyl equivalent weight from about 500 to about 2000.

In general, the resulting oligomeric polyols will have a hydroxyl number from about 20 mg KOH/g to about 300 mg KOH/g. Preferably, the oligomeric polyol will have a hydroxyl number at least about 50 mg KOH/g or higher, or at least about 75 mg KOH/g or higher. Preferably, the oligomeric polyol will have a hydroxyl number about 200 mg KOH/g or lower, or about 180 mg KOH/g or lower.

In general, the oligomeric polyol will have a functionality from about 0.5 to about 10. Preferably, the functionality of the oligomeric polyol will be greater than about 1.0, greater than about 1.5, or greater than about 2.0. The functionality of the oligomeric polyol may be up to 6.0, up to 5.0, or up to 3.0.

The preparation of vegetable oil-based oligomerized polyols using a hydroxyl ring opener with a partially epoxidized soybean oil has several advantages. The preparation of partially epoxidized soybean oil requires less epoxidation agents and requires shorter reaction time than the preparation of fully epoxidized oils. The resulting polyols made from partially epoxidized vegetable oils have a number of double bonds that may contribute to low viscosity. A further possible advantage is that oligomerization can be carried out in a controlled manner that may result in polyols of low molecular weight distribution. Another possible advantage is that the resulting oligomerized polyol may have low viscosity. These properties may have a resulting positive effect on properties of products, such as foams, made using the oligomerized polyols.

Oligomeric content may be strongly affected by the catalyst concentration. It has been found that a higher catalyst concentration contributes to the formation of oligomer species of higher weight average molecular weight than 8000. However, at certain catalyst concentrations (such as greater than 0.3%), the reaction conditions result in a gelling of the reactants within less than 20 minutes of reaction time at 100° C.

The use of fluoroboric acid as the acid in the reaction mixture may be advantageous for several reasons. It is believed that at least some amount of the fluoroboric acid added to the reaction mixture deactivates, is consumed, or is incorporated in the reaction mixture over time. This is referred to as self-regulating behavior. When small quantities of fluoroboric acid is used, all of the acid catalyst may self-regulate, and it is not necessary to remove the catalyst from the reaction mixture. In addition, the neutralization step following the oligomerization reaction may not be necessary. Additionally, acid numbers of the resulting oligomeric polyol may be the same with or without the acid being removed following the reaction. The possibility of corrosion problems on the reaction equipment or on downstream equipment may be reduced. Self-regulation may also lead to greater control over the reaction conditions, and might be used to control the resulting oligomer profile of the resulting oligomeric modified vegetable oil-based polyols.

Various embodiments of an oligomeric mixture of a modified fatty acid triglyceride include the following structures:

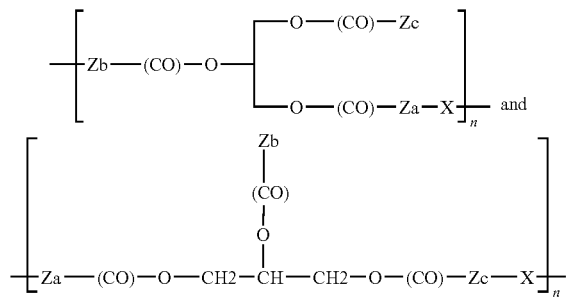

wherein Za, Zb, and Zc independently comprise C15 to C17 straight carbon chains and comprising methylene units, vicinal alkoxy and hydroxy substituted methylene units, 2,3-oxiranyl units, 1,2-ethenediyl units, or combinations thereof, and further comprising an endcap methyl group; and wherein if Za, Zb, or Zc comprises an intermolecular crosslink, that crosslink is provided from the reaction of the hydroxy group or ring opening of the 2,3-oxiranyl group; and wherein n=2-8 for at least 20% of the mixture; and
wherein X=O.

Za, Zb, and Zc are each independently selected from the group consisting of $(CH_2)_7(CH=CH)(CH_2)_7CH_3$, $(CH_2)_7(CH=CH)(CH_2)_7CH_3$, $(CH_2)_7(CHOR-CHOH)(CH_2)_7CH_3$, $(CH_2)_7(CH=CH)CH_2(CHOR-CHOH)(CH_2)_4CH_3$, $(CH_2)_{14}CH_3$, $(CH_2)_7(CHOH-CHOR)CH_2(CHOH-CHOR)CH_2(CH=CH)CH_2CH_3$, $(CH_2)_7(CH=CH)CH_2(CH=CH)CH_2(CHOR-CHOH)CH_2CH_3$, $(CH_2)_7(CH=CH)(CH_2)_7CH_3$, $(CH_2)_7(CH=CH)CH_2(CH=CH)CH_2(CH=CH)CH_2CH_3$, $(CH_2)_7(CH=CH)CH_2(CH=CH)(CH_2)_4CH_3$, $(CH_2)_7(CHOH-$ $(CH_2)_7(CH=CH)(CH_2)_7CH_3$, $(CH_2)_7(CH=CH)(CH_2)_7CH_3$, $(CH_2)_7(CHOR-CHOH)(CH_2)_7CH_3$, $(CH_2)_7(CH=CH)CH_2(CHOR-CHOH)(CH_2)_4CH_3$, $(CH_2)_{14}CH_3$, $(CH_2)_7(CHOH-CHOR)CH_2(CHOH-CHOR)CH_2(CH=CH)CH_2CH_3$, $(CH_2)_7(CH=CH)CH_2(CH=CH)CH_2(CHOR-CHOH)CH_2CH_3$, $(CH_2)_7(CH=CH)(CH_2)_7CH_3$, $(CH_2)_7(CH=CH)CH_2(CH=CH)CH_2(CH=CH)CH_2CH_3$, $(CH_2)_7(CH=CH)CH_2(CH=CH)(CH_2)_4CH_3$, $(CH_2)_7(CHOH-CHOR)CH_2(CHCH)(CH_2)_4CH_3$, or
  \\/
   O $(CH_2)_7(CHCH)CH_2(CHOR-CHOH)CH_2(CH=CH)CH_2CH_3$;
  \\/
   O $CHOH)CH_2(CH=CH)CH_2CH_3$;

wherein R comprises H, $C_1$-$C_{10}$ alkyl groups, $C_7$-$C_{15}$ alkaryl, alkoxyalkyl, or alkylaminoalkyl groups and combinations thereof.

Hydroformylated Vegetable Oil-Based Polyols

A reduced hydroformylated vegetable oil-based polyol may be prepared by adding a vegetable oil and a catalyst to a reactor system, and subjecting the contents to a hydroformylation process. Polyols made by hydroformylation processes may be used in making oligomeric polyols as described above. These reduced hydroformylated polyols may include reduced hydroformylated polyols made by typical hydroformylation processes, or by a new hydroformylation process described herein. This new hydroformylation process provides advantages over conventional hydroformylation processes and is another aspect of the present invention.

Vegetable oil-based polyols may be produced continuously from vegetable oil using a single metal in supported form as the catalyst for both the hydroformylation step and the hydrogenation steps of creating the polyol. After the hydrogenation step, this metal catalyst may be recovered by a simple filtration process and then reused in subsequent reactions.

In the preferred embodiment shown in FIG. 1, a catalyst that is finely-dispersed on a support and is in an organic media is charged into a first reactor 1. The contents of first reactor 1 are agitated under high pressures of syngas and high temperatures for a specific period of time. The contents are then transferred to a second reactor 2 where they are agitated with a specific amount of vegetable oil under high pressures of syngas and high temperatures for a specific period of time. The contents of second reactor 2 are then transferred to a third reactor 3 where they are agitated under certain pressures of hydrogen gas and certain temperatures for a specific period of time. Afterwards, the contents of third reactor 3 undergo filtration in a tower 4, and a catalyst on a support is collected. The collected catalyst-on-support is transferred back to reactor 1 for reuse, and the filtrate is subjected to vacuum stripping in a tower 5 to remove the organic media. The stripped organic media is then fed back to reactor 1 for reuse with the recycled catalyst-on-support. After the filtrate is vacuum stripped, a vegetable oil-based polyol product exits tower 5.

The catalyst may be finely dispersed on a solid support. The solid support may be a fine powder. The catalyst also may be a fine powder form. The catalyst may be mixed with the solid support or may be adsorbed or coated onto the surfaces of the support. Alternatively, a combination of the two methods described above of placing the catalyst on the solid support may be used.

Catalysts suitable for this process include any of the transition metals within Group VIIIB of the periodic chart, i.e., Fe, Ru, Os, Co, Rh, Ir, Ni, Pd, and Pt. Combinations of transitional metals may be used. Preferably, Co and/or Rh is used, and most preferably, Co is used.

Suitable solid supports may include inorganic compounds. Particularly useful supports include materials such as carbon black, alumina, silica, $TiO_2$, MgO, ZnO, $CaCO_3$, $CaSO_4$, $MgSO_4$, or combinations thereof. Preferably, the solid support is carbon black, alumina and/or silica, and more preferably is carbon black. The solid supports can be used in either inactivated or activated form. Preferably, they are used in an activated form.

The metal-to-support ratio can vary widely. Preferably, the metal to support ratio is about 0.1-10 by weight, more preferably about 0.1-2, and most preferably about 0.1-1.

The contents of reactor 1 are agitated under high pressures of syngas and high temperatures to activate the metal. More specifically, this procedure converts the metal into metal carbonyls, which are precursors of the hydroformylation catalysts. Once the metal carbonyls are formed, they are removed from the surfaces due to the extracting effect of the organic media, and thus more metal carbonyls are formed.

The activation of the catalyst is accomplished under higher pressures of syngas and high temperatures for a specific period of time. The ratio of carbon monoxide to hydrogen in the syngas is preferably in the range of about 0.5-2, and more preferably about 1. The pressure of the syngas mixture ranges from about 1000-5000 psig, preferably about 3000-4000 psig. A suitable temperature for the activation ranges from about 100-300° C. and preferably about 150-200° C. The activation takes place in about 1 to 24 hours and preferably in about 1-8 hours.

Preferably, the organic media solubilizes the metal carbonyls formed, and preferably will not solubilize or disintegrate the solid support. The mixture thus remains as a slurry during the entire catalyst activation procedure. Preferably, the organic media shall be compatible with the vegetable oil, the aldehydic intermediate, and the final polyol product. The organic media preferably has a much lower boiling point than the vegetable oil so that it can be recycled readily using vacuum stripping in tower 5.

Suitable organic media include liquid organic compounds. Preferred organic media includes hexanes, heptanes, benzene, toluene, acetone, chloroform, methanol, ethanol, isopropanol, butanol, ethyl acetate, and combinations thereof. Most preferably, the organic media is selected from aromatics and/or hydrocarbons, such as toluene and hexanes.

After activation of the catalyst, the activated catalyst is transferred to reactor 2. Vegetable oil also is added to reactor 2. The activated catalyst and vegetable oil reaction mixture is agitated under pressure and heat to convert the vegetable oil into aldehydic intermediates. The hydroformylation is accomplished under a pressure of syngas of about 1000-5000 psig, preferably about 3000-4000 psig, and at a temperature of about 90-200° C. and preferably about 100-150° C. The molar ratio of carbon monoxide to hydrogen in the syngas is preferably in the range of about 0.5-2 and more preferably about 1. The reaction time for the conversion to aldehydic intermediates should be about 0.5 to 24 hours and preferably about 1-5 hours.

Vegetable and petroleum based oils may be used. After the hydroformylation reaction is completed, the crude product, which contains the aldehydic oil, the organic media, the metal carbonyl catalyst solubilized within, and the solid support dispersed within as a slurry, is transferred directly to reactor 3 where the aldehydic intermediate is hydrogenated in order to produce a polyol. No catalyst/product separation and purification is necessary in this process in contrast to conventional hydroformylation processes.

The hydrogenation of the aldehydic oil is accomplished by agitating the crude hydroformylation product in reactor 3 under certain pressures of hydrogen gas and certain temperatures for a specific period of time. The hydrogen pressure is about 500-2500 psig and preferably about 1000-2000 psig. The hydrogenation reaction temperature is about 120-200° C. and preferably about 150-180° C. The hydrogenation reaction takes place for about 1-5 hours and preferably about 1-3 hours.

Upon completion of the hydrogenation step, the crude product is transferred to tower 4 where it is filtered. The crude product is a slurry of a polyol, organic media, and the catalyst in its metallic form mixed with or coated onto the solid support. The filtration procedure produces two components: a solid component, i.e., the precipitate, containing the catalyst and the support, and a liquid component, i.e., the filtrate, containing the polyol mixed with the organic media. Other catalyst/product separation techniques such as extraction may be used. However, filtration is preferred.

The liquid component containing the polyol and the organic media is subsequently transferred to tower 5 where it undergoes vacuum stripping to separate the polyol from the organic media. The organic media recovered from the stripping process may be recycled by feeding it back into reactor 1.

The recovered catalyst-on-support and the collected organic media can be fed back to reactor 1 separately. It is, however, preferable to mix them together and send them back to reactor 1 in a slurry form so as to avoid any clogging.

The cycle described above can be repeated many times to continuously produce vegetable oil-based polyols are produced continuously from vegetable oils.

The hydroformylation process is more efficient and less costly than conventional hydroformylation processes because it can be accomplished in a shorter amount of time, with less energy, and catalyst/product separation steps and purification steps can be avoided. Further, the polyols produced by the process have less hydroxyl content loss than those formed by conventional processes because the catalyst is active at lower temperatures than 180° C. When the process is performed at temperatures below 180° C., there is substantially no hydroxyl content loss.

Another advantage of the hydroformylation process of the present invention is that the same metal catalyst may be used as the catalyst for the two consecutive steps of the process, i.e., the hydroformylation step and the hydrogenation step. A polyol can be produced directly and continuously by this hydroformylation process of the present invention. As there is no need for using a second metal for the hydrogenation step, fewer steps are required. Preferably, no corrosive reagents will be used in the hydroformylation process of the present invention. A high-pressure post-hydroformylation operation may not be necessary.

Still another advantage of the hydroformylation process of the present invention is that the metal catalyst may be recycled simply by filtration and then the catalyst may be reused in a subsequent reaction. With the catalyst system of the present invention, catalyst deposition on reactor walls or mirror formation is avoided. In addition, waste discharge problems associated with complicated catalyst/product separation and purification steps of conventional processes are avoided, which saves energy. Thus, there is little to no waste discharge. Thus, this process is better to the environment than conventional processes.

The polyols created by this hydroformylation method may be very reactive. Further, when these polyols are used in making coatings, they generally provide a UV resistant backbone for better weathering of coated substrates. Further, these polyols can usually be used as one-component moisture curing adhesives that have very good storage stability.

Another method of making a polyol includes hydroformylating an oil to form an aldehydic intermediate using a catalyst and hydrogenating the aldehydic intermediate to form a polyol using the same catalyst in the presence of a catalyst support. The method may include recovering the catalyst and support following hydrogenation. The recovered catalyst and support may be re-used in hydroformylation and hydrogenation reactions. Suitable oils include vegetable-based oils as well as petroleum-based oils. Suitable catalysts include those described above. This method has the advantages of being able to be used with a wide range of feedstock oils, including blends. In addition, as the same catalyst is used in multiple reactions, the cost of separating or removing catalyst is minimized or eliminated. In addition, as the catalyst is able to be separated and re-cycled for further use, the cost of catalyst may be applied over a larger amount of materials produced. The catalyst is added prior to the hydroformylation reaction. The catalyst support may be added to the hydroformylation reaction, or it may be later added prior to the hydrogenation reactions. Preferably, the support will be added together with the catalyst prior to the hydroformylation reaction.

During the hydrogenation reaction, the catalyst, in the presence of the support, may attach to the support. In various embodiments, at least about 50% of the catalyst present will attach to the catalyst support, at least about 75% of the catalyst present will attach to the support, at least about 90% of the catalyst present will attach to the support, at least about 95% of the catalyst present will attach to the support, at least about 99% of the catalyst will attach to the support, or at least 99.9% of the catalyst present will attach to the support.

Examples of a variety of partially epoxidized vegetable oils, hydroformylated polyols, unsaturated modified vegetable oil-based polyols, and oligomeric polyols are described below.

Example 1

A partially epoxidized soybean oil was prepared as follows:

A 5 liter, 3-neck, round bottom flask was equipped with temperature control, an addition funnel, reflux condenser and stirring. To this reactor system was added: 1500 grams of soybean oil (RBD grade having an Iodine Value of 131 g $I_2$/100 g and a viscosity of 62 mPa s, available from Archer Daniels Midland Company); 225 grams of glacial acetic acid (available from Fisher); and 19 grams of a 50% solution of sulfuric acid in water (available from Aldrich). These ingredients were thoroughly mixed while the reactor system was brought up to a temperature of 70° C. After attaining the temperature set point, 729 grams of a 35% solution of hydrogen peroxide in water (available from Aldrich) was added from a dropping funnel over a period of 30 minutes while maintaining the 70° C. temperature set point and continuing vigorous stirring.

After an additional 45 minutes of reaction time, the contents of the reactor system were transferred to a 3 liter separatory funnel and allowed to cool down. During the cool down period, the water and crude partially epoxidized soybean oil separated into two layers. Product work-up continued by draining off this first water layer and then water washing the crude partially epoxidized soybean oil layer three separate times with 1 liter aliquots of distilled water. The washed partially epoxidized soybean oil was then isolated again and added to an Erlenmeyer flask, and 100 grams of a basic ion exchange resin (Lewatit MP-64 from Bayer) was added. This mixture was stirred for 2 hours to allow neutralization of any remaining acid. The product was then filtered to remove the ion exchange resin and subjected to a low vacuum to remove residual water.

A final partially epoxidized soybean oil product was obtained having an iodine value of 88 g $I_2$/100 g and an epoxy oxygen content number of 1.89%. A summary of the process used and values obtained can be found in Table I on row EX1.

TABLE 1

Partially Epoxidized Vegetable Oils

| Sample | Soybean oil, g (IV = 131) | Acetic acid, g | H2SO4 50%, g (% in water phase) | Temp ° C. (preheat/rxn) | H2O2 35%, g | Ratio DB:AA:H2O2 | Time, min | Ion Resin, g | Epoxy Oxygen Content | Iodine Value | Viscosity (Pa·s at 25 C.) |
|---|---|---|---|---|---|---|---|---|---|---|---|
| EX1 | 1500 | 225 | 19 | 70/70 | 729 | 1:0.5:1 | 45 | 100 | 1.89 | 88 | |
| EX2 | 1500 | 225 | 19 | 70/70 | 729 | 1:0.5:1 | 60 | 100 | 2.74 | 83 | |
| EX3 | 500 | 75 | 6.3 (1) | 70/70 | 147 | 1:0.5:0.6 | 120 | 40 | 3.65 | 65 | |
| EX4 | 500 | 75 | 6.3 (1) | 70/70 | 147 | 1:0.5:0.6 | 60 | 40 | 2.65 | 83 | |
| EX5 | 500 | 75 | 3 (0.5) | 70/70 | 147 | 1:0.5:0.6 | 150 | 40 | 2.96 | 79 | |
| EX6 | 1500 | 225 | 9 | 65/70 | 350 | 1:0.5:0.73 | 140 | 75 | 2.4 | 93 | 0.1 |
| EX7 | 1500 | 225 | 9 | 65/70 | 600 | 1:0.5:0.73 | 3 | 75 | 3.56 | 71 | 0.16 |
| EX8 | 1500 | 225 | 9 | 65/70 | 350 | 1:0.5:0.73 | 3 | 75 | 2.97 | 77 | 0.13 |
| EX9 | 1500 | 225 | 9 | 65/70 | 350 | 1:0.5:0.73 | 150 | 75 | 2.61 | 83 | 0.11 |

Examples 2-5

A series of partially epoxidized soybean oils were prepared according to Example 1, except the time of the reaction and amounts of reactants were changed. The amounts of reactants used and the time reacted are listed in Table 1 on the rows EX2, EX3, EX4, and EX5 for these examples.

The final partially epoxidized soybean oil products obtained had the characteristics as shown in Table 1 on the same rows.

Examples 6-9

A series of partially epoxidized soybean oils were prepared according to Example 1, except the time of the reaction and amounts of reactants were changed. In addition, the hydrogen peroxide was added by a peristaltic pump at a rate of 7.5 ml/min, rather than by a dropping funnel over 30 minutes.

The amounts of reactants used and the time reacted are listed in Table 1 on the rows EX6, EX7, EX8, and EX9 for these examples. The final partially epoxidized soybean oil products obtained had the characteristics as shown in Table 1 on the same rows.

Example 10

A partially epoxidized soybean oil was prepared as follows:

A 2 liter, 3-neck, round bottom flask was equipped with temperature control, an addition funnel, reflux condenser and stirring. To this reactor system was added 500 grams soybean oil (RBD grade having an Iodine Value of 127 g $I_2$/100 g and a viscosity of 60 mPa s, available from Archer Daniels Midland Company); 75 grams of glacial acetic acid; and 6.36 grams of a 50% solution of sulfuric acid in water. The components were thoroughly mixed while the reactor system was brought up to a temperature of 70° C. After attaining the temperature set point, 243 grams of a 35% solution of hydrogen peroxide in water (available from Aldrich) was added from the dropping funnel over a period of 30 minutes while maintaining the 70° C. temperature set point and vigorous stirring. After an additional 4.5 hours of reaction time, the contents of the reactor system were transferred to a 2 liter separatory funnel and allowed to cool down. During the cool down period, the water and crude partially epoxidized soybean oil separated into two layers.

Product work-up continued by draining off this first water layer and then water washing the crude partially epoxidized soybean oil layer three separate times with 1 liter aliquots of distilled water. The washed partially epoxidized soybean oil was then isolated again and 40 grams of a basic ion exchange resin (Lewatit MP-64 from Bayer) was added. This mixture was allowed to stir for 2 hours to allow neutralization of any remaining acid. The product was then filtered to remove the ion exchange resin and subjected to a low vacuum to remove residual water. A final partially epoxidized soybean oil product was obtained having an iodine value of 25.6 g $I_2$/100 g and an epoxy oxygen content number of 5.4%.

Example 11

The preparation of this polyol began with the experimental setup of a 2 liter, 3-neck, round bottom flask equipped with temperature control, an addition funnel, reflux condenser and stirring. To the reactor was now added 330 grams (10.33 moles) of methanol, 83 grams (4.59 moles) of water and 6.731 grams of fluoroboric acid (as a 48% mixture with water, available from Aldrich).

These ingredients were thoroughly mixed while the reactor system was brought to boiling. Then 510 grams (1.72 moles of epoxy groups) of the partially epoxidized soybean oil prepared in Example 6 was quickly added to the vigorously stirred reactor.

After an additional 60 minutes of reaction time, 100 grams of a basic ion exchange resin (Lewatit MP-64 from Bayer) was added to neutralize acids. This mixture was stirred for 1 hour and then allowed to cool down. Product recovery continued by filtering off the solid ion exchange resin and removal of residual water and alcohol by vacuum distillation. The final recovered modified soybean oil-based polyol was a light straw in color and had a hydroxyl number of 192 mg KOH/g and a viscosity of 5,500 mPa s (at 25° C.)

Example 12

A modified soybean oil-based polyol was prepared according to the procedure described in Example 6 of Petrovic, U.S. Pat. No. 6,433,121. Typical features of the product included positive reactivity with isocyanate compounds, terminal hydroxyls that are secondary in nature, a hydroxyl functionality of 3.8, a hydroxyl number of 200 and a 25° C. viscosity in the range of 12,000 mPa s. The product was a light straw in color and revealed a very mild and characteristic odor.

Example 13

A hydroformylated polyol was prepared as follows.

A experimental setup of a 500 milliliter, stainless steel, high-pressure reactor equipped with temperature control and an addition port for gas and stirring was provided. To this reactor system was added 100 grams (0.512 moles of double bonds) of soybean oil commercially purchased from the Archer Daniels Midland Company as the RBD grade and having an Iodine Value of 127 g $I_2$/100 g and a viscosity of 0.06 Pa s.

Also added to the reactor were 5 grams of activated carbon (available from Aldrich) and 5 grams of cobalt carbonyl (available from Strem Chemicals). The reactor was closed up and these ingredients were thoroughly mixed while the reactor system was flushed four times with 50-100 psig of a synthetic gas mixture consisting of an equal molar ratio of hydrogen and carbon monoxide (available from Airgas, Tulsa, Okla.). The reactor was then pressurized to 3,200 psig with the same gas composition and heated while stirring to 120° C., by which time the pressure of the reactor had increased to 4,000 psig.

Stirring continued at 1,000 rpm for 1 hour, after which the pressure was released. The reactor was then flushed four times with 50-100 psig of hydrogen gas (available from Airgas, Tulsa, Okla.), pressurized to 1,800 psig of hydrogen, and the heated to 175° C., by which time the pressure of the reactor had increased to 2,000 psig. The contents of the reactor were stirred at 1,000 rpm for 2 hours under 2,000 psig of hydrogen at 175° C. Upon cooling to 40-50° C. and releasing the gas pressure, the reactor was opened up and the contents were transferred out and filtered through a fritted glass funnel. The black powder collected in the funnel weighed approximately 13 grams while wet, and the yellow viscous liquid filtrate weighted approximately 110 grams. The polyol had 147 mg KOH/g and a 25° C. viscosity of about 4,000 cps at 25° C.

Example 14

A hydroformylated polyol was prepared as follows:

A 500-ml, stainless steel, high-pressure reactor was setup with temperature control, stirring, and addition ports for gas and stirring. 100 grams of soybean oil having an Iodine Value of 127 g $I_2$/100 grams and a viscosity of 60 mPa·s (RBD grade, available from the Archer Daniels Midland Company) was added to the reactor. In addition, 0.129 grams of rhodiumdicarbonyl acetylacetonate (available from Johnson Mathey Co.), and 0.66 grams of triphenyl phosphine (available from Aldrich) were added to the reactor.

The reactor was closed up and the ingredients were thoroughly mixed while the reactor system was flushed with three volumes of a synthetic gas mixture consisting of an equal molar ratio of hydrogen and carbon monoxide. The reactor was then pressurized to 13.4 MPa using the same gas composition.

The reactor system was heated to increase the temperature to 90° C. over a period of 25 minutes while continuing the mix the ingredients. After 2 hours at 90° C., the temperature of the reactor was decreased to 70° C. The reactor was then flushed with three volumes of hydrogen gas.

The reactor was then sealed and pressurized to 3.4 MPa using hydrogen gas. Using heat and continuing to mix the contents, the reactor content temperature was increased to 130° C. After 30 minutes at 130° C., the reactor was cooled. When the contents of the reactor reached 30° C., the pressure was released, and the reactor opened.

9 grams of Raney nickel (available from Strem Chemicals) and 50 ml of isopropanol (reagent grade, available from Sigma Chemical) were then added to the reactor. The system was then resealed, flushed with three volumes of hydrogen gas, and the pressurized to 4.1 MPa with hydrogen gas. Stirring was initiated, and the temperature raised to 110° C. The reaction continued at these conditions for a period of 5 hours, under a maintained hydrogen pressure of 3-5 MPa.

The reactor was then cooled to room temperature, and the gas pressure released. The reactor contents were then filtered through Celite (available from Fisher Scientific) and then subject to vacuum filtration to remove residual solvent. The final recovered modified soybean oil-based polyol was a light brown liquid having a hydroxyl number of 2200 mg KOH/g and a viscosity of 14,000 mPa·s at 25° C.

TABLE 2

Unsaturated Modified Vegetable Oil-Based Polyols

| Sample | Methanol, g | Unsat. epoxidized soy oil, g | Feed oil | Catalyst HBF4 48%, g | AMC, g | Ratio methanol:epoxy groups | Ion Resin, g |
|--------|-------------|------------------------------|----------|----------------------|--------|----------------------------|--------------|
| EX15 | 80 | 250 | EX2 | 0.7 | 0 | 6:1 | 15 |
| EX16 |  | 250 | EX15 |  | 2.5 |  |  |
| EX17 | 204 | 500 | EX3 | 1.5 | 0.5 | 6:1 | 20 |
| EX18 | 164 | 500 | EX4 | 1.4 | 0.5 | 6:1 | 20 |

TABLE 3

Properties of Unsaturated Modified Vegetable Oil-Based Polyols

| Sample | Hydroxyl Number | Epoxy Oxygen Content | Iodine Value | Acid Number | Viscosity, Pa·s at 25 C. | Water, % | Color | Oligomer to monomer ratio |
|--------|-----------------|----------------------|--------------|-------------|--------------------------|----------|-------|---------------------------|
| EX15 | 98 | 0.01 | 77 | 2.4 | 0.4 |  | Yellow | 21:79 |
| EX16 | 100 | 0.01 | 67 | 2.5 | 0.43 | 0.027 | Dark yellow | 20:80 |
| EX17 | 120 | 0.016 | 61 | 0.372 | 0.43 |  | Yellow | 15:85 |
| EX18 | 94 | 0.013 | 79 | 0.334 | 0.26 |  | Yellow | 16:84 |

Example 15

Polyol preparation began with the experimental setup of a 1 liter, 3-neck, round bottom flask equipped with temperature control, an addition funnel, reflux condenser and stirring. To this reactor system was added 80 grams of methanol and 0.7 grams of fluoroboric acid (as a 48% mixture with water, available from Aldrich). These ingredients were thoroughly mixed while the reactor system was brought to boiling. Then 250 grams of the partially epoxidized soybean oil prepared according to Example 2 was quickly added to the vigorously stirred reactor.

After an additional 40 minutes of reaction time, the mixture was cooled to 50-60° C., and about 15 grams of a basic ion exchange resin (Lewatit MP-64 from Bayer) was added to neutralize the acid. This mixture was stirred for 1 hour and then allowed to cool down. Product recovery continued by filtering off the solid ion exchange resin and removal of residual water and alcohol by vacuum distillation. A summary of the process and amounts of reactants used can be found in Table 2.

A summary of the properties of the resulting unsaturated modified soybean oil-based polyol may be found in Table 3.

Example 16

A 1 liter Erlenmeyer flask was equipped with temperature control, an addition funnel, reflux condenser and stirring. 250 grams of a polyol prepared according to Example 15 and 2.5 grams of ammonium carbonate were added to the flask. The ingredients were thoroughly mixed while the reactor system was brought to 60-70° C.

After 15 minutes of stirring, the contents of the reactor system were transferred to a 1-liter separatory funnel and allowed to cool down. During the cool down period, the water and crude partially epoxidized soybean oil separated into two layers. Product work-up continued by draining off this first water layer and then water washing the crude partially epoxidized soybean oil layer five separate times with 500 milliliter aliquots of distilled water. The product was then subjected to a low vacuum to remove residual water. A summary may be found in Table 2.

The final recovered unsaturated modified soybean oil-based polyol had the properties as shown in Table 3.

Examples 17 & 18

Polyols were prepared by following the procedure according to Examples 15 and 16, except using the amounts of reactants and time as listed in Table 2 on the rows EX17 and EX18. The final recovered unsaturated modified soybean oil-based polyols had the properties as found in Table 3.

Example 19

An oligomeric polyol was prepared as follows:

A 1 liter, 3-neck, round bottom flask was equipped with temperature control, an addition funnel, reflux condenser and stirring. To the reactor was added 63 grams of a polyol prepared according to Example 13 and 0.5 grams of fluoroboric acid (as a 48% mixture with water, available from Aldrich). These ingredients were thoroughly mixed while the reactor system was brought to 100° C. Then 150 grams of a partially epoxidized soybean oil prepared according to Example 1 was quickly added to the vigorously stirred reactor.

After an additional 40 minutes of reaction time, the system was cooled down to 50° C. and 10 grams of a basic ion exchange resin (Lewatit MP-64 from Bayer) was added to neutralize acids. This mixture was stirred for 1 hour and then filtered to remove the ion exchange resin. Product recovery continued with removal of residual water by vacuum distillation. A summary of the process and amounts of reactants used can be found in Table 4.

The final recovered oligomeric polyol was a light straw in color and had the properties as shown in Table 5.

TABLE 4

Oligomeric Polyols

| Sample | Starting Material | Starting Material, g | Hydroxyl ring opener | Hydroxyl ring opener, g | Ratio OH:epoxy groups | Catalyst HBF4 48%, g (%) | MeOH, g | 2nd Catalyst (HBF4), g | Water, g | Ion Resin, g | AMC, g |
|---|---|---|---|---|---|---|---|---|---|---|---|
| EX19 | EX1 | 150 | EX13 | 63 | 1:1 | 0.5 (0.1%) | | | | 10 | |
| EX20 | EX2 | 200 | EX12 | 50 | 1:2.2 | 0.5 (0.1%) | 75 | 0.1 | 30 | 15 | 0.275 |
| EX21 | EX2 | 367 | EX12 | 100 | 1:2.2 | 1 (0.1%) | 75 | 0.1 | 30 | 15 | 0.275 |

TABLE 5

Oligomeric Polyols Properties

| Sample | OH number | EOC | Iodine Value | Acid number | Viscosity, Pa·s @ 25 C. | Water, % | Color | Oligomer:Monomer Ratio |
|---|---|---|---|---|---|---|---|---|
| EX19 | 89 | | | 4.3 | 2.3 | | Light Straw | |
| EX 20 | 106 | 0.08 | 57 | 0.34 | 1.4 | 0.051 | Yellow | 47:53 |
| EX 21 | 102 | 0.016 | 57 | 0.34 | 1.6 | | Yellow | 46:54 |

Example 20

A 1 liter, 3-neck, round bottom flask was equipped with temperature control, an addition funnel, reflux condenser, nitrogen purge, and stirring. To the reactor was added 50 grams of a polyol prepared according to Example 12, 0.1% BHT, and 0.5 grams of fluoroboric acid (as a 48% mixture with water, available from Aldrich). These ingredients were thoroughly mixed while the reactor system was brought to 100° C. Then, 200 grams of a partially epoxidized soybean oil prepared according to Example 2 was quickly added to the vigorously stirred reactor, and allowed to react for an additional 30 minutes.

An alcohol mixture (prepared by mixing 75 g of methanol (certified ACS, available from Fisher) and 0.1 g of fluoroboric acid solution (48% in water, available from Aldrich), was added to the reaction flask and the mixture allowed to react for 120 minutes. Then, 30 grams of water was added to the reactor. After an additional 30 minutes of reaction time, the system was cooled down to 50° C. and 15 grams of a basic ion exchange resin (Lewatit MP-64 from Bayer) was added to neutralize acids. This mixture was stirred for 1 hour and then filtered to remove the ion exchange resin, and residual water was removed by vacuum distillation.

230 grams of the prepared oligomeric polyol mixture was transferred to another flask, and 0.275 g of ammonium carbonate (available from Fisher) was dispersed in 1 ml distilled water and added to the flask. This mixture was then mixed for a few minutes. After filtering, the sample was heated to 80-90° C. and exposed to low vacuum using a roto-evaporator (60 min. at ~1 mm Hg). A summary of the process and amounts of reactants used can be found in Table 4.

The resultant oligomeric polyol had the properties as shown in Table 5.

Example 21

An oligomeric polyol was prepared according to the procedure of Example 20, except using the amounts of reactants and time as listed in Table 4 for the row "EX21." The resulting oligomeric polyol had the characteristics as shown in Table 5.

Example 22

The preparation of this oligomeric polyol began with the experimental setup of a 2 liter, 3-neck, round bottom flask equipped with temperature control (water bath), reflux condenser and mechanical stirrer. To this reactor system was added 35.5 grams of methanol (certified A.C.S., available from Fisher) and 1.12 grams of tetrafluoroboric acid (as a 48% water solution, available from Aldrich). These ingredients were thoroughly mixed while the reactor system was brought up to a temperature of 50° C. After attaining the temperature set point, 400 grams of an epoxidized soybean oil ("Flexol," available from Union Carbide) was added to the reactor. Vigorous stirring continued and the reactor temperature was increased to 90° C. After 30 minutes of reaction at these conditions, an additional 100 grams of epoxidized soybean oil ("Flexol") was added to the reactor and the reaction continued for an additional 3 hours.

The reactor was then cooled down to 60° C. and 15 grams of a basic ion exchange resin (Lewatit MP-64 from Bayer) was added. This mixture was allowed to stir for 1 hour to neutralize any remaining acid. The product was then filtered to remove the ion exchange resin and subjected to a low vacuum to remove residual water and solvent.

A summary of the preparation parameters may be found on Table 6 for the row EX22.

The final recovered oligomeric modified soybean oil-based polyol was a light straw in color and had the properties as shown in Table 7 for the row EX22. In addition, the polyol under GPC analysis showed the following composition: 47% monomer; 12% dimer; 8% trimer; and 33% tetramer & high oligomers.

TABLE 6

Processing Parameters - Oligomeric Polyols

| Sample | Methanol, g (molar ratio methanol to epoxy groups) | HBF4, g (%) | Preheat, deg C. | First Addition - Epoxidized Soybean Oil, g | Soybean Oil Temp., deg C. | Temp. Increase to | Reaction Temp. (Bath), deg C. | Additional Intermediate Steps | Final Reaction Time, min | Neutralization, g (Lewatite MP-64) |
|---|---|---|---|---|---|---|---|---|---|---|
| EX22 | 35.5 g (0.53 to 1) | 1.12 g (0.1%) | 50 | 400 | 23 | 90 | 90 | after 30 minutes of reaction time, an additional 100 g of epoxidized soybean oil is added | 180 | 15 |
| EX23 | 26.8 g (0.4 to 1) | 1.10 g (0.1%) | 40 | 400 | 23 | 115 | 90 | after 30 minutes of reaction time, an additional 100 g of epoxidized soybean oil is added | 60 | 16 |
| EX24 | 30.15 g (0.45 to 1) | 1.10 g (0.1%) | 40 | 400 | 23 | 100 | 95 | after 30 minutes of reaction time, an additional 100 g of epoxidized soybean oil is added | 60 | 16 |
| EX25 | 26.80 g (0.4 to 1) | 1.10 g (0.1%) | 40 | 450 | 23 | 100 | 95 | after 30 minutes of reaction time, an additional 50 g of epoxidized soybean oil is added | 60 | 16 |

TABLE 6-continued

Processing Parameters - Oligomeric Polyols

| Sample | Methanol, g (molar ratio methanol to epoxy groups) | HBF4, g (%) | Preheat, deg C. | First Addition - Epoxidized Soybean Oil, g | Soybean Oil Temp., deg C. | Temp. Increase to | Reaction Temp. (Bath), deg C. | Additional Intermediate Steps | Final Reaction Time, min | Neutralization, g (Lewatite MP-64) |
|---|---|---|---|---|---|---|---|---|---|---|
| EX26 | 26.8 g (0.4 to 1) | 1.10 g (0.1%) | 40 | 300 | 23 | 120 | 90 | reaction time, an additional 100 g of epoxidized soybean oil is added, after another 60 minutes of reaction time, an additional 100 g of epoxidized soybean oil is added | 60 | 16 |

TABLE 7

Oligomeric Polyols Properties

| Sample | OH number | EOC | Acid number | Viscosity, Pa·s @ 25 C. | Water, % | Oligomer: Monomer Ratio |
|---|---|---|---|---|---|---|
| EX22 | 82.68 | 3.07 | 0.49 | 5.7 | | 53:47 |
| EX23 | 70.41 | 3.43 | 0.39 | 4.49 | 0.056 | 52:48 |
| EX24 | 71.19 | 3.46 | 0.72 | 3.98 | 0.028 | 51:49 |
| EX25 | 70.68 | 3.38 | 0.39 | 6.7 | 0.028 | 59:41 |
| EX26 | 72.52 | 3.72 | 0.43 | 3.87 | 0.036 | 44:56 |

Example 23

An oligomeric polyol was prepared according to the following procedure:

A reactor system was setup including a 2 liter, 3-neck, round bottom flask equipped with temperature control (water bath), reflux condenser and mechanical stirrer. 26.8 g of methanol (0.838 mol) and 1.10 g of 48% water solution of $HBF_4$ catalyst were added into the flask. Sufficient catalyst was added to obtain a catalyst concentration of 0.1% of the total weight of the reactants. Sufficient methanol was added to obtain a molar ratio of methanol to epoxy of 0.4 to 1. The mixture was heated to 40° C. and a first portion of 400 g of epoxidized soybean oil (1.675 mol of epoxy groups) was added to the flask (80% of the total amount to be added). The reaction started very quickly and the temperature of the reaction mixture jumps up to 115° C., followed by very strong boiling for several seconds. Then, the temperature of reaction mixture decreased and the boiling intensity decreased. The temperature of the water bath was increased to 90° C. and the reaction continued. After 30 minutes, 100 g (0.419 mol) of epoxidized soybean oil was added into the flask with the other components (this is the remaining 20% of the total to be add). After addition, the reaction continued.

After an additional 60 minutes, 16 g of an ion-exchange resin (Lewatit MP-64), in the amount of 3% of the total reaction mixture weight was added into reactor to neutralize the acidic components. At this same time, about 2-3 mL of distilled water and 100 mL toluene were added to improve neutralization and dilute the reaction mixture. Neutralization continued for 60 minutes at a temperature of roughly 60° C. After 60 minutes, the ion-exchange resin was separated from the liquid part by filtration through paper filter (porosity: coarse). Thereafter, the solvent and water were removed by vacuum distillation (Rotavapor) for a period of 5 hours. For the first 2 hours, an oilless vacuum pump was used, while the following 3 hours was conducted under a very high vacuum using an oil vacuum pump. The temperature of the water bath during this process was set to 90° C.

A summary of the preparation parameters may be found on Table 6 for the row EX23.

The final recovered oligomeric modified soybean oil-based polyol had the properties as shown in Table 7 for the row EX23. In addition, the polyol under GPC analysis showed the following composition: 48% monomer; 11% dimer; 7% trimer; 34% tetramer & higher oligomers. The number-average molecular weight determined by vapor pressure osmometry (VPO) was 1678 g/mol and the functionality of the oligomeric polyol was 2.1.

Example 24-26

A series of oligomeric polyols were prepared according to the procedure as described in Example 23. However, each had minor differences, as shown on Table 6.

EX24: The final recovered oligomeric modified soybean oil-based polyol had the properties as shown in Table 7 for the row EX24. In addition, the polyol produced in EX24 under GPC analysis showed the following composition: 49% monomer; 11% dimer; 7% trimer; 33% tetramer & higher oligomers. The number-average molecular weight determined by vapor pressure osmometry (VPO) was 1755 g/mol and the functionality of the oligomeric polyol was 2.35.

EX25: The final recovered oligomeric modified soybean oil-based polyol had the properties as shown in Table 7 for the row EX25. In addition, the polyol under GPC analysis showed the following composition: 41% monomer; 12% dimer; 8% trimer; 39% tetramer & higher oligomers.

EX26: The final recovered oligomeric modified soybean oil-based polyol had the properties as shown in Table 7 for the row EX26. In addition, the polyol under GPC analysis showed the following composition: 56% monomer; 9% dimer; 6% trimer; 29% tetramer & higher oligomers. The number-average molecular weight determined by vapor pressure osmometry (VPO) was 1505 g/mol and the functionality of the oligomeric polyol was 1.95.

Examples 27-44

Another series of oligomeric polyols were prepared according to the procedure as described in Example 23. However, in these examples, all of the epoxidized vegetable oil was added in the initial addition of epoxidized vegetable oil, and no second addition of epoxidized vegetable oil occurred.

The differences in the conditions used are shown on Table 8, on the appropriate row, which shows the various processing parameters used.

The final recovered oligomeric modified soybean oil-based polyols had the properties as shown in Table 9 for the appropriate row.

TABLE 8

Processing Parameters - Oligomeric Polyols (EX27–EX44)

| Sample | Methanol, g (molar ratio methanol to epoxy groups) | HBF4, g (%) | Preheat, deg C. | First Addition - Epoxidized Soybean Oil, g | Soybean Oil Temp., deg C. | Temp. Increase to | Reaction Temp. (Bath), deg C. | Final Reaction Time, min | Neutralization, g (Lewatite MP-64) |
|---|---|---|---|---|---|---|---|---|---|
| EX27 | 26.8 g (0.4 to 1) | 1.10 g (0.1%) | 40 | 500 | 23 | 95 | 90 | 90 | 16 |
| EX28 | 30.15 g (0.45 to 1) | 1.10 g (0.1%) | 40 | 500 | 23 | 90 | 90 | 90 | 16 |
| EX29 | 26.8 g (0.4 to 1) | 0.77 g (0.07%) | 40 | 500 | 40 | 84 | 90 | 180 | 16 |
| EX30 | 26.8 g (0.4 to 1) | 0.77 g (0.07%) | 40 | 500 | 60 | 89 | 90 | 60 | 16 |
| EX31 | 26.8 g (0.4 to 1) | 0.55 g (0.05%) | 40 | 500 | 40 | 69 | 90 | 60 | 16 |
| EX32 | 26.8 g (0.4 to 1) | 0.55 g (0.05%) | 40 | 500 | 60 | 78 | 90 | 60 | 16 |
| EX33 | 26.8 g (0.4 to 1) | 0.55 g (0.05%) | 23 | 500 | 23 | 51 | 70 | 60 | 10 |
| EX34 | 26.8 g (0.4 to 1) | 0.66 g (0.06%) | 23 | 500 | 23 | 61 | 70 | 60 | 10 |
| EX35 | 30.15 g (0.45 to 1) | 0.55 g (0.05%) | 23 | 500 | 23 | 50 | 70 | 60 | 10 |
| EX36 | 30.15 g (0.45 to 1) | 0.66 g (0.06%) | 23 | 500 | 23 | 57 | 70 | 60 | 10 |
| EX37 | 33.5 g (0.5 to 1) | 0.56 g (0.05%) | 23 | 500 | 23 | 45 | 70 | 60 | 10 |
| EX38 | 33.5 g (0.5 to 1) | 0.67 g (0.06%) | 23 | 500 | 23 | 58 | 70 | 60 | 10 |
| EX39 | 26.8 g (0.4 to 1) | 0.77 g (0.07%) | 23 | 500 | 23 | 61 | 70 | 60 | 10 |
| EX40 | 20.1 g (0.3 to 1) | 0.54 g (0.05%) | 23 | 500 | 23 | 44 | 70 | 60 | 10 |
| EX41 | 23.45 g (0.35 to 1) | 0.55 g (0.05%) | 23 | 500 | 23 | 45 | 70 | 60 | 10 |
| EX42 | 22.1 g (0.33 to 1) | 0.54 g (0.05%) | 23 | 500 | 23 | 47 | 70 | 60 | 5 |
| EX43 | 22.1 g (0.33 to 1) | 0.54 g (0.05%) | 23 | 500 | 23 | 39 | 70 | 60 | 0 |
| EX44 | 22.1 g (0.33 to 1) | 0.54 g (0.05%) | 23 | 500 | 23 | 42 | 70 | 60 | 0 |

TABLE 9

Oligomeric Polyol Properties (EX27–EX44)

| Sample | OH number | EOC | Acid number | Viscosity, Pa·s @ 25 C. | Water, % | Monomer | Dimer | Trimer | Tetramer & Higher | Number Avg MW | Functionality |
|---|---|---|---|---|---|---|---|---|---|---|---|
| EX27 | 67.97 | 3.39 | 0.46 | 7.54 | 0.029 | 37% | 12% | 8% | 43% | 1949 | 2.36 |
| EX28 | 79.78 | 3.17 | 0.43 | 7.59 | 0.043 | 37% | 13% | 8% | 42% | 2000 | 2.80 |
| EX29 | 66.61 | 3.8 | 0.4 | 4.11 | 0.035 | 43% | 13% | 8% | 36% | | |
| EX30 | 63.18 | 4.16 | 0.23 | 2.55 | 0.01 | 50% | 13% | 9% | 28% | | |
| EX31 | 52.25 | 4.25 | 0.19 | 2.46 | 0.028 | 49% | 14% | 9% | 28% | | |
| EX32 | 49.34 | 4.61 | 0.19 | 1.68 | 0.021 | 59% | 14% | 9% | 21% | | |
| EX33 | 61.99 | 3.84 | 0.2 | 3.63 | 0 | 44% | 13% | 9% | 34% | 1518 | 1.68 |
| EX34 | 70.03 | 3.64 | 0.25 | 5.5 | 0 | 40% | 13% | 8% | 39% | | |
| EX35 | 76.2 | 3.57 | 0.31 | 4.9 | 0 | 43% | 14% | 9% | 34% | | |
| EX36 | 79.84 | 3.68 | 0.33 | 6.9 | 0.018 | 39% | 13% | 8% | 40% | | |
| EX37 | 81.62 | 3.44 | 0.32 | 7.5 | 0.027 | 38% | 13% | 9% | 40% | | |
| EX38 | 85.64 | 3.01 | 0.35 | 8.8 | 0.021 | 37% | 14% | 8% | 41% | | |
| EX39 | 71.94 | 3.78 | 0.34 | 9.15 | 0.007 | 36% | 12% | 7% | 45% | | |
| EX40 | 52.74 | 4.39 | 0.29 | 3.78 | 0.021 | 46% | 12% | 8% | 34% | 1750 | 1.64 |
| EX41 | 62.05 | 4.12 | 0.33 | 4.5 | 0.019 | 43% | 13% | 85% | 36% | 1810 | 2.00 |
| EX42 | 53.77 | 4.23 | 0.33 | 4 | 0.064 | 45% | 13% | 8% | 34% | 1668 | 1.60 |
| EX43 | 56.16 | 4.26 | 0.34 | 4.45 | 0 | 43% | 12% | 8% | 37% | 1698 | 1.70 |
| EX44 | 57.19 | 4.11 | 0.34 | 3.99 | 0.027 | 45% | 12% | 8% | 35% | 1849 | 1.88 |

Example 45

A 1 liter, 3-neck, round bottom flask was equipped with temperature control, an addition funnel, reflux condenser, nitrogen purge, and stirring. To the reactor was added 24 grams of a polyol prepared according to Example 14 and 0.1 grams of fluoroboric acid (as a 48% mixture with water, available from Aldrich). These ingredients were thoroughly mixed while the reactor system was brought to 100° C. Then, 82.5 grams of a partially epoxidized soybean oil prepared according to Example 1 was quickly added to the vigorously stirred reactor, and allowed to react for an additional 60 minutes.

After reacting, the system was cooled down to 50° C. and 10 grams of a basic ion exchange resin (Lewatit MP-64 from Bayer) was added to neutralize acids. This mixture was stirred for 1 hour and then filtered to remove the ion exchange resin, and residual water was removed by vacuum distillation. A summary of the process and amounts of reactants used can be found in Table 10.

The resultant oligomeric polyol had the properties as shown in Table 11.

Examples 46-49

A series of oligomeric polyols were prepared according to the procedure of Example 23, except using the amounts of reactants and time as listed in Table 10 for the rows EX46, EX47, EX48, and EX49.

In the EX 46 sample, the epoxidized vegetable oil was washed and dried prior to use in the reaction. The oil was washed using an equivalent volume of warm distilled water, and then dried by being placed in a flask with 10 grams of anhydrous sodium sulfate.

In EX47, EX48, and EX49, the epoxidized vegetable oil was washed using an equivalent volume of warm distilled water prior to addition to the reaction.

The resulting oligomeric polyols had the characteristics as shown in Table 11.

Example 50

An oligomeric polyol was prepared according to the following:

TABLE 10

Oligomeric Polyol Reactions

| Sample | Starting Material | Starting Material, g | Starting Material Treatment | Hydroxyl ring opener | Hydroxyl ring opener, g | Ratio OH:epoxy groups | Catalyst HBF4 48%, g % | Reaction Time, min |
|---|---|---|---|---|---|---|---|---|
| EX45 | EX1 | 82.5 | Non-washed | EX14 | 24 | 1:1 | 0.1 (0.1%) | 60 |
| EX46 | EX1 | 53 | Washed & dried | EX14 | 15 | 1:1 | 0.1 (0.1%) | 60 |
| EX47 | EX1 | 173 | Washed | EX14 | 49 | 1:1 | 0.2 (0.1%) | 60 |
| EX48 | EX1 | 150 | Washed | EX13 | 63 | 1:1 | 0.2 (0.1%) | 60 |
| EX49 | EX1 | 150 | Washed | EX12 | 58 | 1:1 | 0.2 (0.1%) | 60 |

TABLE 11

Oligomeric Polyols Properties

| Sample | OH number | Acid number | Viscosity, Pa.s @ 25 C |
|---|---|---|---|
| EX 45 | 103 | 5.8 | 0.7 |
| EX 46 | 97 | 1.2 | 0.6 |
| EX 47 | 113 | 3.2 | 2.5 |
| EX 48 | 89 | 4.3 | 2.3 |
| EX 49 | 115 | 2.1 | 0.7 |

A 250-ml, 3-neck, round bottom flask was equipped with temperature control, an addition funnel, reflux condenser, nitrogen purge, and stirring. To the reactor was added 10 grams of a polyol prepared according to Example 12, 0 grams of water, and 0.05 grams of fluoroboric acid. These ingredients were thoroughly mixed while the reactor system was brought to 100° C.

After 90 minutes of reaction time the mixture was sampled and then an additional 0.1% of catalyst, $HBF_4$, was added. A summary of the reaction is shown in Table 12, and a summary of the properties of the resulting oligomeric polyol is shown in Table 13.

TABLE 12

Oligomer Polyols

| Sample | Starting Material | Starting Material, g | Hydroxyl ring opener | Hydroxyl ring opener, g | Ratio OH:epoxy groups | Catalyst HBF4 48%, g (%) | Water, g | Rxn Time, min |
|---|---|---|---|---|---|---|---|---|
| EX50 | EX2 | 40 | EX12 | 10 | 1:2.2 | 0.05 (0.1%) |  | 90 |
| EX51 | EX2 | 40 | EX12 | 10 | 1:2.2 | 0.10 (0.2%) |  | 90 |
| EX52 | EX2 | 40 | EX12 | 10 | 1:2.2 | 0.15 (0.3%) |  | 10 |
| EX53 | EX2 | 40 | EX12 | 10 | 1:2.2 | 15 (30%) | 1 | 150 |
| EX54 | EX2 | 40 | EX12 | 10 | 1:2.2 | 20 (40%) | 0.5 | 150 |

TABLE 13

Ratio of the oligomer species in sample

| Sample (Min) | Viscosity, Pa.s @ 25° C. | Ratio oligomers to monomer |
|---|---|---|
| EX 50, 90 min | 0.70 | 45:55 |
| EX 50, After 0.1% catalyst added | 3.80 | 65:35 |
| EX 51 | 2.4 | 60:40 |
| EX 53, 30 min | 1.2 | 44:56 |
| EX 53, 60 min | 1.2 | 44:56 |
| EX 53, 150 mm | 1.2 | 44:56 |
| EX 54, 30 min | 1.8 | 56:44 |
| EX 54, 60 mm | 1.8 | 57:43 |
| EX 54, 90 min | 1.8 | 57:43 |
| EX 54, 120 min | 1.8 | 58:42 |

Examples 51-54

A series of oligomeric polyols were prepared according to the procedure of Example 50, except using the amounts of reactants and time as listed in Table 12 for the rows EX51, EX52, EX53, and EX54.

A sample of EX51 was taken at 90 minutes.

The reaction in EX52 was very fast, and the reaction mixture gelled after 10 minutes of reaction, and no sample was taken.

A sample of EX53 was taken at 30, 60, and 150 minutes.

Samples of EX 54 were taken at 30, 60, 90, and 120 minutes.

The results from the samples taken are shown Table 13

Example 55

The preparation of this oligomeric polyol began with the experimental setup of a 2 liter, 3-neck, round bottom flask equipped with an addition funnel, reflux condenser and stirring. To this reactor system was added 100 grams of the polyol prepared according to Example 12. The flask was immersed in a boiling water bath. After a few minutes, 1.0 grams of fluoroboric acid (as a 48% mixture with water, available from Aldrich) was added to the flask and mixed. After several minutes of mixing, 400 grams of the polyol prepared according to Example 2 was added to the flask. After 30 mintues of reaction, 80 grams of methanol (certified ACSS grade, available from Aldrich) was added to the flask. After 120 minutes, 20 grams of water was added to the flask. After an additional 30 minutes, the flask was cooled to 50°-60° C. and around 30 grams of basic ion exchange resin (Lewatit MP-64, available from Bayer) was added and stirred for one hour. Then, filtration was carried out by a pressure filter to remove the resin, and excess water and methanol were removed by low pressure vacuum. A summary of amounts of reactants and process used appears in Table 14.

The final recovered oligomeric polyol had the properties as shown in Table 15 for the row EX55. In addition, the polyol under GPC analysis exhibited the composition profile as shown in Table 16, under the column EX55.

TABLE 14

Oligomeric Polyol Formulations

| Sample | Starting Material | Starting Material, g | Hydroxyl ring opener | Hydroxyl ring opener, g | Catalyst HBF4, g (%) | BHT antioxidant, g (%) | Ratio OH:epoxy groups |
|---|---|---|---|---|---|---|---|
| EX55 | EX2 | 400 | EX12 | 100 | 1 (0.1%) | — | 1:2.2 |
| EX56 | EX2 | 160 | EX12 | 40 | 0.8 (0.2%) | — | 1:2.2 |
| EX57 | EX2 | 240 | EX12 | 60 | 1.2 (0.2%) | 0.3 (0.1%) | 1:2.2 |

TABLE 15

Oligomeric Polyol Properties

| Sample | OH number | EOC | Iodine Value | Acid number | Water, % | Viscosity, Pa·s @ 25 C. | Oligomer:Monomer |
|---|---|---|---|---|---|---|---|
| EX55 | 103 | 0.18 | 57 | 0.7 | 0.03 | 1.7 | 51:49 |
| EX56 | 86 | 0.26 | 57 | 0.8 | 0.035 | 6.4 | 60:40 |
| EX57 | 93 | 0.07 | 57 | 0.9 | 0.037 | 3.3 | 63:37 |

TABLE 16

Oligomeric Polyol Molecular Weight Distribution

| Molecular species | Oligomer content, % | | |
|---|---|---|---|
| | EX 55 | EX 56 | EX 57 |
| High oligomers | 12.88 | 28.58 | 29.38 |
| Tetramers | 14.88 | 12.1 | 13.82 |
| Trimers | 9.5 | 8.02 | 8.15 |
| Dimers | 13.71 | 11.23 | 11.97 |
| Monomers | 49.03 | 40.06 | 36.68 |

Example 56

An oligomeric polyol was prepared according to the procedure of Example 55, except using the amounts of reactants as listed in Table 14 for the row EX56. The final recovered oligomeric polyol had the properties as shown in Table 15 for the row "EX56." In addition, the polyol under GPC analysis exhibited the composition profile as shown in Table 16, under the column EX56.

Example 57

The preparation of this oligomeric polyol began with the experimental setup of a 1 liter, 3-neck, round bottom flask equipped with an addition funnel, reflux condenser, nitrogen inlet, and stirring. To this reactor system was added 60 grams of the polyol prepared according to Example 12 and 0.3 grams of BHT antioxidant (2,6-Di-tert-butyl-4-methylphenol, available from Aldrich). The flask was immersed in a boiling water bath. The reaction mixture was constantly maintained under a nitrogen atmosphere throughout the reaction.

After a few minutes, 1.2 grams of fluoroboric acid (as a 48% mixture with water, available from Aldrich) was added to the reactor and mixed. After several minutes of mixing, 240 grams of the polyol prepared according to Example 2 was added to the flask. After 30 mintues of reaction, 90 grams of methanol (certified ACS grade, available from Aldrich) and 0.18 grams of additional HBF4 catalyst was added to the reactor. After 60 minutes, the reactor was cooled to 50°-60° C. and around 15 grams of basic ion exchange resin (Lewatit MP-64, available from Bayer) was added and stirred for one hour. Then, filtration was carried out by a pressure filter to remove the resin, and excess water and methanol were removed by low pressure vacuum. A summary of amounts of reactants and process used appears in Table 14.

The final recovered oligomeric polyol had the properties as shown in Table 15 for the row EX57. In addition, the polyol under GPC analysis exhibited the composition profile as shown in Table 16, under the column EX57.

Example 58

An oligomeric polyol was prepared according to the following:

A 250-ml, 3-neck, round bottom flask was equipped with temperature control, an addition funnel, reflux condenser, and stirring. 60 grams of an epoxidized soy oil prepared according to Example 6, 0.72 grams of methanol (ACS grade, available from Aldrich), and 0.12 grams of fluoroboric acid were added to the reactor. These ingredients were thoroughly and continually mixed as the reactor was placed into a water bath and brought to 60° C.

After 180 minutes of reaction time, 15 grams of methanol and an additional 0.1 grams of $HBF_4$ were added to the reactor. After an additional 30 minutes, the reactor was cooled to 50-60° C., and 5 grams of Lewatit MP-64 was added. The mixture was stirred for 2 hours, and the resulting polyol was filtered to remove the resin, and then vacuumed for 30 min at low vacuum and 30 minutes at high vacuum. A summary of amounts of reactants used is shown on Table 17.

The oligomeric polyol formed had the properties as shown in Table 18, with properties reported for the sample at 180 minutes, and the final polyol composition.

Example 59

An oligomeric polyol was prepared according to the procedure of Example 58, except using the amounts of reactants and temperature as listed in Table 17 for the row EX59. The oligomeric polyol had the properties as shown in Table 18 for samples at 180 minutes, and a final sample.

Example 60

An oligomeric polyol was prepared according to the procedure of Example 58, except using the amounts of reactants and temperature as listed in Table 17 for the row EX60, and the experiment was discontinued after 60 minutes of reaction time, at which time a sample was taken. The later steps of Example 58 were not completed. The oligomeric polyol had the properties as shown in Table 18, with the time at which the sample was taken.

TABLE 17

Oligomeric Polyol Formulations - Temp. and Catalyst Concentration Variation

| Sample | MeOH, g | Unsaturated epoxidized soy oil | Unsaturated epoxidized soy oil, g | Ratio methanol:epoxy groups | Catalyst HBF$_4$, g (%) | Temp. ° C. |
|---|---|---|---|---|---|---|
| EX58 | 0.72 | EX6 | 60 | 0.25:1 | 0.12 (0.1%) | 60 |
| EX59 | 0.72 | EX6 | 60 | 0.25:1 | 0.12 (0.1%) | 70 |
| EX60 | 0.72 | EX6 | 60 | 0.25:1 | 0.12 (0.1%) | 80 |
| EX61 | 0.72 | EX6 | 60 | 0.25:1 | 0.12 (0.1%) | 90 |
| EX62 | 0.6 | EX6 | 50 | 0.25:1 | 0.2 | 60 |
| EX63 | 0.6 | EX6 | 50 | 0.25:1 | 0.3 | 60 |

Example 61

An oligomeric polyol was prepared according to the procedure of Example 58, except using the amounts of reactants and temperature as listed in Table 17 for the row EX61. The experiment was discontinued after 60 minutes of reaction time, at which time a sample was taken. The oligomeric polyol had the properties as shown in Table 18, with the time at which the sample was taken.

Example 62

An oligomeric polyol was prepared according to the procedure of Example 58, except using the amounts of reactants as listed in Table 17 for the row EX62. The experiment was discontinued after 120 minutes of reaction time, at which time a sample was taken. The oligomeric polyol had the properties as shown in Table 18, with the time at which the sample was taken.

TABLE 18

Oligomeric Polyol Properties - Temp. and Catalyst Concentration Variation

| Sample | OH number | Acid number | EOC | Viscosity, Pa·s @ 25 C. | Oligomer, % | Monomer, % |
|---|---|---|---|---|---|---|
| EX58, 180 min |  | 0.63 | 1.34 | 0.34 | 44 | 56 |
| EX58 final | 65 |  | 0.005 | 0.59 | 47 | 53 |
| EX59, 180 min |  | 0.58 | 1.83 | 0.24 | 28 | 72 |
| EX59 final | 78 |  | 0.005 | 0.4 | 33 | 67 |
| EX60, 60 min |  | 0.49 | 1.82 | 0.23 | 26 | 74 |
| EX61, 60 min |  | 0.48 | 1.6 | 0.24 | 35 | 65 |
| EX62, 120 min |  | 0.86 | 0.66 | 1.06 | 60 | 40 |
| EX63, 120 min |  | 1.41 | 0.06 | 3.82 | 69 | 31 |
| EX64, 120 min |  | 1.84 | 0.005 | 8.6 | 72 | 28 |

Example 63

An oligomeric polyol was prepared according to the procedure of Example 58, except using the amounts of reactants as listed in Table 17 for the row EX63. In addition, a jacketed flask was used for temperature control, rather than a water bath, and the temperature jumped to 82° C. at the beginning of the reaction, and was then brought back down to 60° C. The experiment was discontinued after 120 minutes of reaction time, at which time a sample was taken. The oligomeric polyol had the properties as shown in Table 18, along with the time at which the sample was taken.

Example 64

An oligomeric polyol was prepared according to the procedure of Example 58, except using the amounts of reactants as listed in Table 17 for the row EX64. A water bath was used, and the temperature jumped to 65° C. at the beginning of the reaction, and was then brought back down to 60° C. The experiment was discontinued after 120 minutes of reaction time, at which time a sample was taken. The oligomeric polyol had the properties as shown in Table 18, along with the time at which the sample was taken.

TABLE 19

Oligomeric Polyol Formulations - Temp. and Catalyst Concentration Variation

| Sample | MeOH, g | Unsaturated epoxidized soy oil | Unsaturated epoxidized soy oil, g | Ratio methanol:epoxy groups | Catalyst HBF$_4$, g (%) | Temp. ° C. |
|---|---|---|---|---|---|---|
| EX65 | 0 | EX6 | 50 | 0 | 0.1 (0.1%) | 60 |
| EX66 | 0 | EX6 | 50 | 0 | 0.3 (0.3%) | 60 |

TABLE 19-continued

Oligomeric Polyol Formulations - Temp. and Catalyst Concentration Variation

| Sample | Unsaturated epoxidized soy oil | Unsaturated epoxidized soy oil, g | Ratio methanol:epoxy groups | Catalyst $HBF_4$, g (%) | Temp. ° C. |
|---|---|---|---|---|---|
| | MEK, g | | | | |
| EX67 | 50 | EX6 | 50 | 0 | 0.2 (0.1%) | 60 |

Example 65

An oligomeric polyol was prepared according to the procedure of Example 58, except using the amounts of reactants as listed in Table 19 for the row EX65. The oligomeric polyol had the properties as shown in Table 20, along with the time at which the sample was taken. The last sample was taken at 75 minutes.

Example 66

An oligomeric polyol was prepared according to the procedure of Example 58, except using the amounts of reactants as listed in Table 19 for the row EX66. The oligomeric polyol had the properties as shown in Table 20, along with the time at which the sample was taken. The last sample was taken at 90 minutes.

TABLE 20

Polyol Characteristics (EX 65 & EX 66)

| | EX 65 | | EX 66 | |
|---|---|---|---|---|
| Reaction time | Acid Number | EOC | Acid Number | EOC |
| 0 | 0.63 | 2.43 | | 2.43 |
| 3 | 0.53 | 2.31 | | 0.96 |
| 5 | 0.62 | 2.05 | | 0.59 |
| 10 | 0.63 | 2.09 | | 0.58 |
| 15 | 0.61 | 2.09 | | 0.57 |
| 30 | 0.64 | 2.05 | | 0.56 |
| 60 | 0.65 | 2.03 | | 0.61 |
| 75 | 0.65 | 1.98 | | |
| 90 | | | | 0.56 |
| | A lot of gel in all specimens | | The specimens gelled completely | |

Example 67

An oligomeric polyol was prepared according to the procedure of Example 58, except using the amounts of reactants as listed in Table 19 for the row EX67. As shown, MEK (available from Aldrich) was added to the reaction rather than methanol. The oligomeric polyol had the properties as shown in Table 21, along with the time at which the sample was taken. The last sample was taken at 160 minutes.

TABLE 21

Polyol Characteristics (EX 67)

| Sample EX 67, Reaction time (min) | Acid number | EOC | Oligomer, % | Monomer, % |
|---|---|---|---|---|
| 0 | 0.64 | 1.2 | 92 | 8 |
| 3 | 0.69 | 0.24 | 60 | 40 |
| 5 | 0.73 | 0.28 | 60 | 40 |
| 23 | 0.68 | 0.27 | 60 | 40 |
| 60 | 0.71 | 0.31 | 60 | 40 |
| 160 | 0.72 | 0.24 | 60 | 40 |

Example 68

An unsaturated oligomeric polyol was prepared according to the following:

A 1-L, three-neck round bottom jacketed reaction flask was equipped with a thermometer, addition funnel, reflux condenser, temperature control, and a mechanical stirrer.

100 g of the unsaturated modified epoxidized soybean oil prepared according to the procedure of Example 8 was preheated to 60° C. and added to the flask. Then, 1.2 g of methanol with an initial catalyst amount of 0.2 g of $HBF_4$ was added to the flask. The reaction temperature jumped up to about 65° C. in 1 minute after addition of all components, but after a few minutes, the reaction temperature dropped to 60° C.

After 10 minutes of continued reaction with vigorous stirring of the mixture, 36 g of methanol mixed with an additional 0.1 g of $HBF_4$ was added to the flask, and the reaction continued. After an additional 20 minutes of reaction, 4 g of Lewatit MP-64 was added to the reaction mixture. The mixture was stirred for an additional 2 hours without heating. After this, the product was filtered and vacuumed for 30 min at low vacuum and 30 minutes at high vacuum.

A summary of amounts of reactants used is shown on Table 22. The oligomeric polyol formed had the properties as shown in Table 23 and Table 24.

Examples 69-76

A series of unsaturated oligomeric polyols were prepared according to the procedure of example 68, except using the reactants, amounts, and conditions as shown on Table 22. The unsaturated oligomeric polyols formed had the properties as shown in Table 23 and Table 24.

TABLE 22

Formulation of Unsaturated Oligomeric Polyols

| Sample | Methanol, g | Unsaturated epoxidized soy oil | Unsaturated epoxidized soy oil, g | Ratio methanol:epoxy groups | Initial Catalyst $HBF_4$, g (% of total) | Lewatit MP-64 |
|---|---|---|---|---|---|---|
| EX68 | 1.2 | EX8 | 100 | 0.20:1 | 0.2 (0.1%) | 4 |
| EX69 | 1.2 | EX8 | 100 | 0.20:1 | 0.4 (0.2%) | 8 |
| EX70 | 1.2 | EX8 | 100 | 0.20:1 | 0.6 (0.3%) | 12 |
| EX71 | 1.2 | EX7 | 100 | 0.17:1 | 0.2 (0.1%) | 4 |
| EX72 | 1.2 | EX7 | 100 | 0.17:1 | 0.4 (0.2%) | 8 |
| EX73 | 1.2 | EX7 | 100 | 0.17:1 | 0.6 (0.3%) | 12 |
| EX74 | 1.2 | EX9 | 100 | 0.23:1 | 0.2 (0.1%) | 4 |
| EX75 | 1.2 | EX9 | 100 | 0.23:1 | 0.4 (0.2%) | 8 |
| EX76 | 1.2 | EX9 | 100 | 0.23:1 | 0.6 (0.3%) | 12 |

TABLE 23

Characteristics of Unsaturated Oligomeric Polyols

| Sample | OH number | EOC | Viscosity, Pa·s @ 25 C. | Oligomer, % | Monomer, % | Equivalent Weight |
|---|---|---|---|---|---|---|
| EX68 | 73 | 0.015 | 0.65 | 44 | 56 | 768 |
| EX69 | 74 | 0.011 | 1.15 | 57 | 43 | 758 |
| EX70 | 68 | 0.01 | 4 | 66 | 34 | 837 |
| EX71 | 78 | 0.097 | 1.26 | 53 | 47 | 719 |
| EX72 | 89 | 0.017 | 3.05 | 62 | 38 | 630 |
| EX73 | 66 | 0.017 | 7.5 | 62 | 38 | 850 |
| EX74 | 70 | 0.01 | 0.56 | 45 | 55 | 802 |
| EX75 | 77 | 0.016 | 0.85 | 56 | 44 | 728 |
| EX76 | 60 | 0.04 | 2.7 | 60 | 40 | 935 |

TABLE 24

Molecular Weight Distribution by GPC and Functionality of the Unsaturated Oligomeric Polyols

| Sample | Monomer, % | Dimer, % | Trimer, % | Tetramer, % | Pentamer, % | High Oligomer, % | Very high oligomer, % | Mn | Functionality, F |
|---|---|---|---|---|---|---|---|---|---|
| EX68 | 56 | 12 | 8 | 6 | 12 | 6 | 0 | 1207 | 1.57 |
| EX69 | 43 | 12 | 8 | 6 | 18 | 13 | 0 | 1716 | 2.26 |
| EX70 | 34 | 10 | 7 | 6 | 15 | 18 | 11 | 3776 | 4.51 |
| EX71 | 47 | 13 | 8 | 8 | 13 | 12 | 0 | 1521 | 2.12 |
| EX72 | 38 | 11 | 7 | 6 | 14 | 21 | 4 | 2059 | 3.27 |
| EX73 | 38 | 11 | 7 | 5 | 12 | 17 | 9 | 2034 | 2.39 |
| EX74 | 55 | 14 | 16 | 12 | 4 | 0 | 0 | 1215 | 1.33 |
| EX75 | 44 | 14 | 9 | 9 | 11 | 13 | 0 | 929 | 1.28 |
| EX76 | 35 | 11 | 7 | 6 | 12 | 22 | 8 | 1259 | 1.35 |

Example 77

The black powder (approx 13 grams) collected in Example 13 was returned into the 500-mL pressure reactor. 50 mL of toluene (Fisher Scientific, Pittsburgh, Pa.) was added to the reactor, and the reactor sealed. The interior was flushed 4 times with 50-100 psig of syngas (1:1 $CO/H_2$). Afterwards, the reactor was pressurized to 2,700 psig with syngas and heated to 180° C. while stirring. At this time, the pressure of the reactor had reached 4,000 psig. The contents of the reactor were stirred at 1,000 rpm for 5 hours under 4,000 psig of syngas at 180° C. After 5 hours, the contents were cooled, under a syngas pressure of 3,500-4,000 psig, to room temperature and the pressure was released. 100 grams of soybean oil (RBD grade, available from Archer Daniels Midland) was added and the reactor sealed again. The contents were flushed 4 times with 50-100 psig of syngas. Afterwards, the reactor was pressurized to 3,200 psig of syngas and heated while stirring to 120° C. Upon heating, the pressure of the reactor reached 4,000 psig. The contents of the reactor were stirred at 1,000 rpm for 1.5-2 hours under 4,000 psig of syngas at 120° C., after which the pressure was released. The reactor was then flushed 4 times with 50-100 psig of hydrogen gas, pressurized to 1,800 psig of hydrogen, and heated to 175° C., by which time the pressure of the reactor had reached 2,000 psig. The contents of the reactor were stirred at 1,000 rpm for 2 hours under 2,000 psig of hydrogen at 175° C. Upon cooling to 40-50° C., the pressure of the reactor was released, and the contents were transferred out and filtered through a fritted-glass funnel. The black powder collected in the funnel weighed approx. 12 grams while wet, and the yellow viscous liquid filtrate weighed approx. 110 grams. The polyols present in the yellow viscous liquid had a hydroxyl content of 161 mg KOH/g (67% yield) and a viscosity of ca. 4,000 cps at 25° C.

Example 78

The procedure described in Example 77 was followed using the catalyst recovered from Example 77. The polyol obtained had a hydroxyl content of 161 mg KOH/g (67% yield) and a viscosity of ca. 4,000 cps at 25° C.

Example 79

A black powder produced according to the method of Example 13 was placed back into the 500-mL pressure reactor, along with 50 mL of toluene. The reactor was sealed and the contents flushed 4 times with 50-100 psig of syngas. Afterwards, the reactor was pressurized to 2,700 psig of syngas and heated while stirring to 180° C., by which time the pressure of the reactor had reached 4,000 psig. The contents of the reactor were stirred at 1,000 rpm for 5 hours under 4,000 psig of syngas at 180° C. The contents of the reactor were then cooled, under a syngas pressure of 3,500-4,000 psig, to room temperature, and the pressure was released. 100 grams of RBD grade soybean oil was added to the reactor. The reactor was sealed again and the contents flushed 4 times with 50-100 psig of syngas. Afterwards, the reactor was pressurized to 3,200 psig of syngas and heated while stirring to 120° C., by which time the pressure of the reactor had reached 4,000 psig. The contents of the reactor were stirred at 1,000 rpm for 1.5-2 hours under 4,000 psig of syngas at 120° C. The contents of the reactor were then cooled to room temperature and the pressure was released. The crude product was filtered on a fritted-glass funnel, and an aldehydic oil was obtained along with some catalyst solubilized within. The Atomic Absorption analysis for cobalt of the filtrate showed that 54% of the original catalyst was present as the carbonyl form.

Example 80

The procedure described in Example 13 was followed except the amount of carbon was 1 gram. The black powder collected weighed 3.5 grams while wet.

Example 81

The procedure described in Example 79 was followed using the black powder recovered from Example 80. The Atomic Absorption analysis for cobalt of the filtrate showed that only 8% of the original catalyst was present as the carbonyl form.

Example 82

The procedure described in Example 13 was followed except the amount of carbon was 10 grams. The black powder collected weighed 25.0 grams while wet.

Example 83

The procedure described in Example 79 was followed using the black powder recovered from Example 82. The Atomic Absorption analysis for cobalt of the filtrate showed that 63% of the original catalyst was present as the carbonyl form.

Example 84

Into a 500-mL stainless steel stirred pressure reactor was loaded with 100 grams of RDM grade soybean oil, 2.5 grams activated carbon, 2.5 grams cobalt carbonyl. The reactor was sealed and the contents flushed 4 times with 50-100 psig of syngas. Afterwards, the reactor was pressurized to 3,200 psig of syngas and heated while stirring to 120° C., by which time the pressure of the reactor reached 4,000 psig. The contents of the reactor were stirred at 1,000 rpm for 1 hour under 4,000 psig of syngas at 120° C., after which the pressure was released. The reactor was then flushed 4 times with 50-100 psig of hydrogen gas, pressurized to 1,800 psig of hydrogen, and heated to 150° C., by which time the pressure of the reactor had reached 2,000 psig. The contents of the reactor were stirred at 1,000 rpm for 3 hours under 2,000 psig of hydrogen at 150° C. The reactor contents were then cooled to 40-50° C. and the pressure of the reactor was released. The contents were transferred out and filtered. FT-IR analysis of the viscous liquid filtrate showed that 24% of the aldehyde from hydroformylation was still present.

Examples 85-88

These examples demonstrate that the polyol quality is significantly dependent on the syngas-to-substrate volume ratio. The head space of the reactor represents the volume of the syngas available for the hydroformylation reaction to take place. Although more syngas is supplied during the reaction, this process is dispersion controlled (i.e., the dispersion of gases to the liquid is much slower than the reaction rate).

The reactions shown in Table 25 were carried out by following the procedure described in Example 13, except that no carbon support is used. 5 parts of cobalt carbonyl was used in all these reactions. In contrast to Example 13, a cobalt mirror surface was formed on the inner wall of the reactor in all these examples.

TABLE 25

| Example | Substrate volume (ml) | Head space (ml) | Syngas-to-oil volume ratio | Polyol OH# (mg KOH/g) | Polyol yield | Polyol viscosity (cps at 25° C.) |
|---|---|---|---|---|---|---|
| 85 | 250 | 150 | 0.6 | 79 | 33% | 2,400 |
| 86 | 100 | 200 | 2.0 | 164 | 68% | 2,300 |
| 87 | 70 | 230 | 3.3 | 174 | 72% | 4,200 |
| 88 | 50 | 250 | 5.0 | 171 | 71% | 3,700 |

Examples 89-91

These examples demonstrate that the polyol quality is dependent on the hydrogenation time period. The highest yield of polyol was produced when the hydrogenation was carried out for 2 hours at 175° C.

These reactions shown in Table 26 were carried out following the procedure described in Example 13, except that no carbon support was used. 5 grams of cobalt carbonyl is used in all these reactions. A cobalt mirror surface was formed on the inner surface of the reactor in all these examples.

TABLE 26

| Example | Hydrogenation time (hour) | Polyol OH # (mg KOH/g) | Polyol yield | Polyol viscosity (cps at 25° C.) |
|---|---|---|---|---|
| 89 | 1 | 157 | 65% | 3,500 |
| 90 | 2 | 164 | 68% | 2,300 |
| 91 | 3 | 150 | 62% | 3,900 |

Example 92

A polyol was produced by the following procedure:

61 g of methanol and 0.44 g of HBF4 were added in a three-neck round bottom jacketed reaction flask equipped with a reflux condenser and a mechanical stirrer. The mixture was preheated to the boiling temperature of approx 65° C. 150 g of a partially epoxidized soybean oil having EOC=3.39 and IV=69 was added to the mixture and the mixture was strongly stirred. The reaction was allowed to proceed for 40 minutes. Then, the heating was stopped and 10 g of Lewatit MP-64 was added. The mixture was stirred for an additional 2 hours without heating. The neutralized mixture was filtered and vacuumed by rota-vapor. The resulting polyol had an OH#=119, EOC=0.006, viscosity=1.3 Pa·S (at 25° C.), an acid value=0.52, and calculated iodine value=65. The number average molecular weight of the polyol was 1135, the weight average molecular weight of the polyol was 1332, and the functionality was 2.34.

A battery of color tests were run on the sample and a water sample, including the Gardner Color Scale Test. The results are shown in Table 27.

TABLE 27

| | Polyol Color Test Results. | | | | |
|---|---|---|---|---|---|
| Sample | L* | a* | b* | Gardner Color | APHA-20 mm |
| Water Standard | 96.73 | −0.23 | 0.07 | 0 | −0.6 |
| EX92 | 96.33 | −2.72 | 15.83 | 1.8 | 243.9 |

Examples 93

A series of oligomeric polyols were prepared via a ring opening reaction performed in a three-necked round bottom glass reactor prepared with very strong stirring and a reflux condenser. Catalyst solution was carefully added into a hydroformylated polyol prepared according to the procedure of Example 13. The mixture was preheated to 60° C. and strongly mixed. The temperature was raised to 90-95° C. and an amount of an epoxidized soybean oil ("Flexol," available from Union Carbide) was slowly added into the reactor. The mixture was then allowed to react for a specified time. The amount of reactants and reaction time is shown on Table 28.

TABLE 28

| Oligomeric polyols incorporating hydroformylated vegetable oil | | | | | |
|---|---|---|---|---|---|
| Sample ID | HF polyol, g | ESBO, g | HBF4 48%, g (%) | EPOXY/OH molar ratio | Reaction time, h |
| EX93 | 100 | 49.6 | 0.16(0.05%) | 0.5 | 3 |
| EX94 | 100 | 49.6 | 0.31(0.1%) | 0.5 | 3 |
| EX95 | 75 | 74.4 | 0.31(0.1%) | 1 | 3 |
| EX96 | 70 | 104.2 | 0.36(0.1%) | 1.5 | 3 |
| EX97 | 100 | 50.2 | 0.31(0.1%) | 0.5 | 11 |
| EX98 | 100 | 50.6 | 0.31(0.1%) | 0.5 | 10 |

Following the reaction, the mixture was neutralized by mixing with Lewatite MP 64 resin for 1 hour at 60° C., after which the reaction mixture was diluted with ether and the Lewatite resin was filtered off. The solvents were removed from the polyol using rotavapor (45 min at 70° C. oilless pump and 90 minutes at 90° C. high vacuum pump).

The resulting polyols had the properties as shown in Table 29.

TABLE 29

| Properties of oligomeric polyols incorporating hydroformylated vegetable oil | | | | | |
|---|---|---|---|---|---|
| Sample | Viscosity, Pa.s | EOC (polyol), % | EOC, % | Epoxy reacted, % | OH #, mgKOH/g | Oligomers, % |
| EX93 | 2.91 | 2.22 | 2.24 | 1 | 158 | 5 |
| EX94 | 4.67 | 1.88 | 2.24 | 16 | 158.78 | 25.94 |
| EX95 | 4.34 | 2.67 | 3.36 | 21 | 125.46 | 42.52 |
| EX96 | 3.7 | 3.2 | 4.0 | 21 | 101.79 | 45.89 |
| EX97 | 6.77 | 1.76 | 2.24 | 21 | 153.0 | 39.75 |
| EX98 | 8.04 | 1.73 | 2.25 | 23 | 155.9 | 42.27 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of making an oligomeric modified vegetable oil-based polyol, comprising reacting a mixture comprising an epoxidized vegetable oil and a ring opener to form an oligomeric modified vegetable oil-based polyol, wherein a molar ratio of hydroxyl groups present in the ring opener to epoxy groups present in the epoxidized vegetable oil is from about 0.1 to about 1.0 and wherein the oligomeric modified vegetable oil-based polyol comprises at least about 40% oligomers, and a viscosity at 25° C. of less than about 8 Pa·s.

2. The method of claim 1, wherein the mixture further comprises an acid.

3. The method of claim 2, wherein the acid comprises fluoroboric acid.

4. The method of claim 3, wherein the fluoroboric acid is self-regulating.

5. The method of claim 2, wherein the acid comprises carboxylic acids, Lewis acids, and Bronsted-Lowry inorganic acids.

6. The method of claim 1, wherein the ring opener comprises hydroxyl groups, and wherein the molar ratio of hydroxyl groups present in the ring opener to epoxy groups present in the epoxidized vegetable oil is from 0.25 to 0.50.

7. The method of claim 1, wherein the oligomeric modified vegetable oil-based polyol comprises at least about 50% oligomers.

8. The method of claim 1, wherein the ring opener comprises alcohol.

9. The method of claim 8, wherein the alcohol comprises a branched alcohol.

10. The method of claim 8, wherein the alcohol comprises a linear alcohol.

11. The method of claim 1, further comprising:
blending petrochemical-based polyols with the epoxidized vegetable oil and the ring opener so that said petrochemical-based polyols also undergo the polymerization reaction.

12. The method of claim 1, wherein the ring opener comprises a vegetable-oil based polyol.

13. The method of claim 1, wherein the epoxidized vegetable oil comprises essentially full epoxidation of all unsaturated groups present in the vegetable oil.

14. The method of claim 1, wherein the epoxidized vegetable oil comprises less than about 90% epoxidation of all unsaturated groups present in the vegetable oil.

15. The method of claim 1, wherein the epoxidized vegetable oil comprises less than about 80% epoxidation of all unsaturated groups present in the vegetable oil.

16. The method of claim 1, wherein the oligomeric modified vegetable oil-based polyol has a functionality from about 1.0 to about 6.0.

17. The method of claim 1, wherein the oligomeric modified vegetable oil-based polyol has a hydroxyl number from about 20 to about 300 mg KOH/g polyol.

18. The method of claim 1, wherein the oligomeric modified vegetable oil-based polyol has a number average molecular weight from about 1,200 to about 8,000.

19. The method of claim 1, wherein the oligomeric modified vegetable oil-based polyol has a weight average molecular weight from about 1500 to about 50,000.

20. The method of claim 1, wherein the epoxidized vegetable oil is formed in situ from a vegetable oil in the presence of an acid.

21. The method of claim 11, wherein the oligomeric modified vegetable oil-based polyol has residual epoxide functionality.

22. The method of claim 1, wherein the oligomeric modified vegetable oil-based polyol has residual epoxide functionality and has residual olefinic functionality.

23. The method of claim 1, wherein the ring opener comprises hydroxyl groups, and wherein the molar ratio of hydroxyl groups present in the ring opener to epoxy groups present in the epoxidized vegetable oil is from about 0.3 to about 0.6.

24. The method of claim 1, wherein the method comprises:
ring-opening the epoxidized vegetable oil using an alcohol and an acid catalyst; and
reacting an epoxidized vegetable oil with the ring-opened epoxidized vegetable oil.

25. The method of claim 1, wherein the ring opener is selected from the group consisting of methanol, ethanol, propanol, isopropanol, and butanol.

* * * * *